US008586311B2

(12) United States Patent
Danenberg

(10) Patent No.: US 8,586,311 B2
(45) Date of Patent: *Nov. 19, 2013

(54) METHOD OF DETERMINING A CHEMOTHERAPEUTIC REGIMEN BASED ON ERCC1 AND TS EXPRESSION

(75) Inventor: Kathleen D. Danenberg, Altadena, CA (US)

(73) Assignee: Response Genetics, Inc., Los Angeles, CA (US)

( * ) Notice: Subject to any disclaimer, the term of this patent is extended or adjusted under 35 U.S.C. 154(b) by 363 days.

This patent is subject to a terminal disclaimer.

(21) Appl. No.: 12/774,261

(22) Filed: May 5, 2010

(65) Prior Publication Data

US 2011/0212981 A1    Sep. 1, 2011

Related U.S. Application Data

(60) Continuation of application No. 12/502,753, filed on Jul. 14, 2009, now Pat. No. 7,732,144, which is a continuation of application No. 11/341,515, filed on Jan. 30, 2006, now Pat. No. 7,560,543, which is a division of application No. 09/877,178, filed on Jun. 11, 2001, now Pat. No. 7,049,059.

(60) Provisional application No. 60/250,358, filed on Dec. 1, 2000, provisional application No. 60/250,471, filed on Dec. 4, 2000.

(51) Int. Cl.
    *C12Q 1/68* (2006.01)
    *C12P 19/34* (2006.01)

(52) U.S. Cl.
    USPC ..................... 435/6.12; 435/91.2

(58) Field of Classification Search
    None
    See application file for complete search history.

(56) References Cited

U.S. PATENT DOCUMENTS

| | | | |
|---|---|---|---|
| 4,830,969 A | 5/1989 | Holmes | |
| 4,843,155 A | 6/1989 | Chomczynski | |
| 5,128,247 A | 7/1992 | Koller | |
| 5,284,940 A | 2/1994 | Lin et al. | |
| 5,346,994 A | 9/1994 | Chomczynski | |
| 5,502,166 A | 3/1996 | Mishina | |
| 5,620,852 A | 4/1997 | Lin et al. | |
| 5,637,687 A | 6/1997 | Wiggins | |
| 5,643,767 A | 7/1997 | Fischetti et al. | |
| 5,654,179 A | 8/1997 | Lin | |
| 5,672,696 A | 9/1997 | Wang et al. | |
| 5,705,336 A | 1/1998 | Reed et al. | |
| 5,707,802 A | 1/1998 | Sandhu et al. | |
| 5,728,822 A | 3/1998 | Macfarlane | |
| 5,777,099 A | 7/1998 | Mehra | |
| 5,945,515 A | 8/1999 | Chomczynski | |
| 5,952,202 A | 9/1999 | Aoyagi et al. | |
| 5,989,857 A | 11/1999 | Mundschenk | |
| 5,998,151 A | 12/1999 | Johnston et al. | |
| 6,010,700 A | 1/2000 | Richt | |
| 6,043,354 A | 3/2000 | Hillebrand et al. | |
| 6,204,375 B1 | 3/2001 | Lader | |
| 6,207,408 B1 | 3/2001 | Essenfeld et al. | |
| 6,248,535 B1 | 6/2001 | Danenberg et al. | |
| 6,518,416 B1 | 2/2003 | Danenberg | |
| 6,613,518 B2 | 9/2003 | Danenberg et al. | |
| 7,049,059 B2 | 5/2006 | Danenberg | |
| 7,732,144 B2 * | 6/2010 | Danenberg | 435/6.12 |
| 2002/0090642 A1 | 7/2002 | Johnston et al. | |

FOREIGN PATENT DOCUMENTS

| | | |
|---|---|---|
| CN | 1 420 927 | 5/2003 |
| EP | 0 290 144 | 9/1988 |
| JP | 2003-525033 | 8/2003 |
| JP | 2004-518429 | 6/2004 |
| WO | WO 90/02203 | 3/1990 |
| WO | WO 95/28489 A | 10/1995 |
| WO | WO 97/05248 | 2/1997 |
| WO | WO 97/35034 | 9/1997 |
| WO | WO 98/41648 | 9/1998 |
| WO | 00/56920 | 9/2000 |
| WO | WO 01/46402 | 6/2001 |

OTHER PUBLICATIONS

Ardalan, B., et al., "Thymidylate Synthase Gene Expression in Normal and Malignant Colorectal Tissues: Relation to in vivo Response and Survival," Proceedings of the American Association for Cancer Research, vol. 37, Abstract No. 1376 (Mar. 1996).
Aschele, C., et al., "Thymidylate Synthase Protein Expression in Primary Colorectal Cancer Compared with the Corresponding Distant Metastases and Relationship with the Clinical Response to 5-Fluorouracil," Clinical Cancer Research, 6: 4797-4802 (2000).
Ausubel, F.M., ed., Current Protocols in Molecular Biology, John Wiley & Sons, Inc., vol. 1.; Strauss, W. M., "Preparation of Genomic DNA from Mammalian Tissue," Unit 2.2, pp. 2.2.1-2.2.3 (1998).
Ausubel, F.M., ed., Current Protocols in Molecular Biology, John Wiley & Sons, Inc., vol. 1.; Richards, E., et al., "Preparation of Genomic DNA from Plant Tissue," Unit 2.3, pp. 2.3.1-2.3.7 (1994).
Ausubel, F.M., ed., Current Protocols in Molecular Biology, John Wiley & Sons, Inc., vol. 1.;Wilson, K., "Preparation of Genomic DNA from Bacteria," Unit 2.4, pp. 2.4.1-2.4.5 (1994).
Banerjee, S.K., et al., "Microwave-Based DNA Extraction from Paraffin-Embedded Tissue for PCR Amplification," BioTechniques, vol. 18, No. 5, pp. 768, 770, 772, 773 (1995).
Beck, A., et al., "A Role for Dihydropyrimidine Dehydrogenase and Thymidylate Synthase in Tumour Sensitivity to Fluorouracil," European Journal of Cancer, 30A(10):1517-1522 (1994).

(Continued)

Primary Examiner — Christopher M Babic
Assistant Examiner — David Thomas
(74) Attorney, Agent, or Firm — Kenyon & Kenyon LLP

(57) ABSTRACT

The present invention relates to prognostic methods which are useful in medicine, particularly cancer chemotherapy. The object of the invention to provide a method for assessing TS and/or ERCC1 expression levels in fixed or fixed and paraffin embedded tissues and prognosticate the probable resistance of a patient's tumor to treatment with 5-FU and oxaliplatin-based therapies by examination of the amount of TS and/or ERCC1 mRNA in a patient's tumor cells and comparing it to a predetermined threshold expression level for those genes. More specifically, the invention provides to oligonucleotide primer pairs ERCC1 and TS and methods comprising their use for detecting levels of ERCC1 and TS mRNA, respectively.

16 Claims, 9 Drawing Sheets

(56) References Cited

OTHER PUBLICATIONS

Benhattar, J., et al., "*p53 Mutations as a Possible Predictor of Response to Chemotherapy in Metastatic Colorectal Carcinomas,*" Int. J. Cancer (Pred. Oncol.), vol. 69, pp. 190-192 (1996).

Britten, et al., "*ERCC1 Expression as a Molecular Marker of Cisplatin Resistance in Human Cervical Tumor Cells,*" Int. J. Cancer 89(5): pp. 453-457 (2000).

Bresters, D., et al., "*Detection of Hepatitis C Viral RNA Sequences in Fresh and Paraffin-Embedded Liver Biopsy Specimens of Non-A, Non-B Hepatitis Patients,*" J. Hepat., vol. 15, pp. 391-395 (1992).

Bresters, D., et al., "*The Duration of Fixation Influences the Yield of HCV cDNA-PCR Products from Formalin-Fixed, Paraffin-Embedded Liver Tissue,*" J. Virol. Method, vol. 48, pp. 267-272 (1994).

Chen, Z., et al., "*Correlation of Cisplatin Sensitivity with Differential Alteration of EGFR Expression in Head and Neck Cancer Cells,*" Anticancer Research 20:899-902 (2000).

Chirgwin, J., M., et al., "*Isolation of Biologically Active Ribonucleic Acid from Sources Enriched in Ribonuclease,*" Biochemistry, vol. 18, No. 24, pp. 5294-5299 (1979).

Chomczynski, P., et al., "*Single-Step Method of RNA Isolation by Acid Guanidinium Thiocyanate-Phenol-Chloroform Extraction,*" Analytical Biochemistry, vol. 162, pp. 156-159 (1987).

Chomczynski, P., "*A Reagent for the Single-Step Simultaneous Isolation of RNA, DNA and Proteins from Cell and Tissue Samples,*" BioTechniques, vol. 15, No. 3, pp. 532-534, 536-537 (1993).

Codegoni, et al., "*Expression of Genes of Potential Importance in the Response to Chemotherapy and DNA Repair in Patients with Ovarian Cancer,*" Gynecol Oncol., Apr.; 65(1): 130-7 (1997).

Coombs, N. J., et al., "*Optimisation of DNA and RNA Extraction from Archival Formalin-Fixed Tissue,*" Nucl. Acids Research, vol. 27, No. 16, pp. i-iii (1999).

Dabholkar, el al., "*Expression of Excision Repair Genes in Nonmalignant Bone Marrow from Cancer Patients,*" Mutat Res., Jan.; 293(2): 151-60 (1993).

Dabholkar, et al., "*ERCC1 and ERCC2 Expression in Malignant Tissues from Ovarian Cancer Patients,*" J Natl Cancer Inst., Oct. 7; 84(19):1512-7 (1992).

Dabholkar, et al., "*Messenger RNA Levels of XPAC and ERCC1 in Ovarian Cancer Tissue Correlate with Response to Platinum-Based Chemotherapy*" J Clin Invest, Aug.; 94(2): 703-8 (1994).

Dakhama, A., et al., "*Amplification of Human β-Actin Gene by the Reverse Transcripase-Polymerase Chain Reaction: Implications for Assessment of RNA from Formalin-Fixed, Paraffin-Embedded Material,*" J. Histochem. and Cytochem., vol. 44, No. 10, pp. 1205-1207 (1996).

Damia, et al., "*Expression of Genes Involved in Nucleotide Excision Repair and Sensitivity to Cisplatin and Melphalan in Human Cancer Cell Lines,*" Eur J Cancer, Oct.; 34(11): 1783-8 (1998).

de Andrés, B., et al., "*Improved Method for mRNA Extraction from Paraffin-Embedded Tissues,*" BioTechniques, vol. 18, No. 1, pp. 42-43 (1995).

Duin Van M, et al., "*Molecular Characterization of the Human Excision Repair Gene ERCC-1: cDNA Cloning and Amino Acid Homology with the Yeast DNA Repair Gene Rad10,*" Cell 44(6): pp. 913-923 (1986).

Eads, C. A., et al., "*CpG Island Hypermethylation in Human Colorectal Tumors is Not Associated with DNA Methyltransferase Overexpression,*" Cancer Research, vol. 59, pp. 2302-2306 (1999).

Edamoto, Y., et al., "*Hepatitis C and B Virus Infections in Hepatocellular Carcinoma,*" Cancer, vol. 77, No. 9, pp. 1787-1791 (1996).

Elder, et al., "*Immunohistochemical Determination of Thymidylate Synthase in Colorectal Cancer-Methodological Studies,*" European Journal of Cancer 33(13): pp. 2278-2281 (1997).

Elder, et al., "*Thymidylate Synthase Expression in Colorectal Cancer: a Prognostic and Predictive Marker of Benefit from Adjuvant Fluorouracil-Based Chemotherapy,*" Journal of Oncology 20(7): pp. 1721-1728 (2002).

Elder, et al., "*Thymidylate Synthase Expression: an Independent Prognostic Factor for Local Recurrence, Distant Metastasis, Disease-Free and Overall Survival in Rectal Cancer,*" Clinical Cancer Research, vol. 6, pp. 1378-1384 (2000).

Elder, et al., "*Immunohistochemically Detected Thymidylate Synthase in Colorectal Cancer: an Independence Prognostic Factor of Survival,*" Clinical Cancer Research, vol. 6, pp. 488-492 (2000).

Etienne M.C., et al., "*Response to Fluorouracil Therapy in Cancer Patients: The Role of Tumoral Dihydropyrimidine Dehydrogenase Activity,*" Journal of Clinical Oncology, 13(7):1663-1670 (1995).

Farrugia, D., et al., "*A Pharmacodynamic (PD) Study of the Thymidylate, Synthase (TS) Inhibitor Tomudex™ in Advanced Colorectal Cancer (CRC),*" Proceedings of the American Association for Cancer Research, Eighty-eighth Annual Meeting (Apr. 12-16, 1997), vol. 38 (1997), Abstract #4132.

Finke, J., et al., "*An Improved Strategy and a Useful Housekeeping Gene for RNA Analysis from Formalin-Fixed, Paraffin-Embedded Tissues by PCR,*" BioTechniques, vol. 14, No. 3, pp. 448-453 (1993).

Gibson, "*A Novel Method for Real Timequantitative RT-PCR,*" Genome Res 6: 995-1001 (1996).

Gilmore, et al., "*The Development and Optimisation of a Quantitative RT-PCR Technique from Formalin-Fixed and Paraffin-Embedded (FFPE) Tissues, Using the Thymidylate Synthase (TS) Gene As a Target,*" American Society of Clinical Oncology: 17: Abstract 2159 (1998).

Godfrey, et al., "*Quantitative mRNA Expression Analysis from Formalin-Fixed, Paraffin-Embedded Tissues Using 5' Nuclease Quantitative Reverse Transcription-Polymerase Chain Reaction,*" J Mol Diagnostic, American Society for Investigative Pathology 2(2): pp. 84-91 (2000).

Goldsworthy, S. M., et al., "*Effects of Fixation on RNA Extraction and Amplification from Laser Capture Microdissected Tissue,*" Molecular Carcinogenesis, vol. 25, pp. 86-91 (1999).

Gorlick, et al., "*Higher Levels of Thymidylate Synthase Gene Expression are Observed in Pulmonary as Compared with Hepatic Metastases of Colorectal Adenocarcinoma,*" J Clin Oncol, Apr.;16(4): 1465-9 (1998).

Greer, C. E., et al., "*PCR Amplification from Paraffin-Embedded Tissues,*" Am. J. Clin. Pathol., vol. No. 95, No. 2, pp. 117-124 (1991).

Gruber, A. D., et al., "*Detection of Bovine Viral Diarrhea Virus RNA in Formalin-Fixed, Paraffin-Embedded Brain Tissue by Nested Polymerase Chain Reaction,*" J. Virol. Methods, vol. 43, pp. 309-319 (1993).

Guerrero, R.B., et al., "*Effects of Formalin Fixation and Prolonged Block Storage on Detection of Hepatitis C Virus RNA in Liver Tissue,*" Diag. Molec. Path., vol. 6, No. 5, pp. 277-281 (1997).

Heid, CA, "*Real Time quantitative PCR,*" Genome Res 6: 986-994 (1996).

Hodges, E., et al., "*Isolation of Nucleic Acid from Paraffin Embedded Tissue for PCR Amplification and Sequencing of TcR Vβ Genes,*" Leuk. Research, vol. 19, No. 3, pp. 183-186 (1995).

Horie, N., et al., "*Functional Analysis and DNA Polymorphism of the Tandemly Repeated Sequences in the 5' terminal Regulatory Region of the Human Gene for Thymidylate Synthase,*" Cell Structure and Function, vol. 20, No. 3, pp. 191-197 (1995).

Horikoshi, T., et al., "*Quantitation of Thymidylate Synthase, Dihydrofolate Reductase, and DT-Diaphorase Gene Expression in Human Tumors using the Polymerase Chain Reaction,*" Cancer Res., vol. 52, pp. 108-116 (1992).

Houze, et al., "*Detection of Thymidylate Synthase Gene Expression Levels in Formalin-Fixed Paraffin Embedded Tissue by Semiquantitative, Nonradioactive Reverse Transcriptase Polymerase China Reaction,*" Tumor Biology 18(1): pp. 53-68 (1997).

Hsuih, T. C. H., et al., "*Novel, Ligation-Dependent PCR Assay for Detection of Hepatitis C Virus in Serum,*" J. Clin. Microbiol., vol. 34, No. 3, pp. 501-507 (1996).

Hughey C. T., et al., "*Genetic Variation in Thymidylate Synthase Confers Resistance to 5-Fluorodeoxyuridine,*" Novel Approaches to Selective Treatments of Human Solid Tumors: Laboratory and Clinical Correlation, edited by Y. M Rustum, Plenum Press, New York, pp. 67-76 (1993).

Ichikawa, et al., "*Expression of Dihydropyrimidine Dehydrogenase (DPD) and Thymidylate Synthase (TS) mRNA in Primary Tumor Predicts the Anti-Tumor Effect in 5-Fluorouracil (FU Rased Chemo-

(56) References Cited

OTHER PUBLICATIONS therapy for Gastrointestinal (GI) Cancer," Proceedings of the American Association for Cancer Research, vol. 42, Abstract No. 3326 (Mar. 2001).

Iqbal S, Lenz HJ, "Determinants of prognosis and response to therapy in colorectal cancer," Curr Oncol Rep., Mar.; 3(2):102-8 (2001).

Ishikawa, et al., Jpn J of Cancer Res 91(1): 105-112, see abstract only (2000).

Iwamoto, K. S., et al., "Feasibility of Using Decades-Old Archival Tissues in Molecular Oncology/Epidmiology," Am. J. Path., vol. 149, No. 2, pp. 399-406 (1996).

Jackman, A. L., et al., "Thymidylate Synthetase Inhibitors: Experimental and Clinical Aspects," Chapter 7 in Experimental and Clinical Progress in Cancer Chemotherapy, F.M. Muggia, ed., Martinus Nijhoff, Boston, pp. 155-210 (1985).

Jiang, Y.-H., et al., "A Rapid RT-PCR Method for Detection of Intact RNA in Formalin-Fixed Paraffin-Embedded Tissues," Nucl. Acids. Res., vol. 23, No. 15, pp. 3071-3072 (1995).

Johnston, P. G., et al., "Thymidylate Synthase Gene and Protein Expression Correlate and Are Associated with Response to 5-Fluorouracil in Human Colorectal and Gastric Tumors," Cancer Research, vol. 55, No. 7, pp. 1407-1412 (1995).

Johnston, et al., "TS Expression from Formalin Fixed Paraffin Embedded (FFPE) Tissues Using Quantitative RT-PCR Correlates with Frozen Tissue Data and Predicts for Response to 5-FU in Metastatic Colorectal Cancers," American Society of Clinical Oncology: Abstract 2383 (1999).

Johnston, et al., "The Role of Thymidylate Synthase Expression in Prognosis and Outcome of Adjuvant Chemotherapy in Patients with Rectal Cancer," Journal of Clinical Oncology 12(12): pp. 2640-2647 (1994).

Kaneda, et al, "Structural and Functional Analysis of the Human Thymidylate Synthase Gene," J Biol Chem 265(33): pp. 20277-20284 (1990).

Kashani-Sabet, et al., "Detection of Drug Resistance in Human Tumors by in vitro Enzymatic Amplification," Cancer Research, vol. 48, pp. 5775-5778 (1998).

Kawakami, K., et al., "Polymorphic Tandem Repeats in the Thymidylate Synthase Gene is Associated with its Protein Expression in Human Gastrointestinal Cancers," Proceedings of the American Society of Clinical Oncology, vol. 17, Abstract No. 1128 (May 1998).

Keyomarsi, K., et al., "Mechanism of the Cytotoxic Synergism of Fluoropyrimidines and Folinic Acid in Mouse Leukemic Cells," J. Biol. Chem., vol. 263, No. 28, pp. 14402-14409 (1988).

Kirihara, et al., "Dihydropyrimidine Dehydrogenase, Multidrug Resistance Associated Protein, and Thymidylate Synthase Gene Expression Levels can Predict 5-fluorouracil Resistance in Human Gastrointestinal Cancer Cells," Int J Oncol., Mar.; 14(3): 551-6 (1999).

Kiyosawa, K., et al., "Interrelationship of Blood Transfusion, Non-A, Non-B Hepatitis and Hepatocellular Carcinoma: Analysis by Detection of Antibody to Hepatitis C Virus," Hepatology, vol. 12, No. 4, pp. 671-675 (1990).

Koopmans, M., et al., "Optimization of Extraction and PCR Amplification of RNA Extracts from Paraffin-Embedded Tissue in Different Fixatives," J. Virological Methods, vol. 43, pp. 189-204 (1993).

Kornmann M. et al., "Thymidylate synthase is a predictor for response and resistance in hepatic artery infusion chemotherapy," Cancer Letters, 118:29-35 (1997).

Leichman et al., "Quantitation of intratumoral thymidylate synthase expression predicts for disseminated colorectal cancer response and resistance to protracted-infusion fluorouracil and weekly leucovorin,". J Clin Oncol., Oct.;15(10): 3223-9 (1997).

Lenz, et al., "p53 Point Mutations and Thymidylate Synthase Messenger RNA levels in Disseminated Colorectal Cancer: An Analysis of Response and Survival," Clin Cancer Res 4: 1243-1250 (1998).

Lenz, et al., "Thymidylate Synthase mRNA Level in Adenocarcinoma of the Stomach: a Predictor for Primary Tumor Response and Overall Survival," J Clin Oncol 14: 176-182 (1995).

Lenz, et al., "p53 and Thymidylate Synthase Gene Expression in Untreated Stage II Colon Cancer: Association with Recurrence, Survival, and Site" Clin Cancer Res 4: 1227-34 (1998).

Li, et al., "Association Between the Level of ERCC-1 Expression and the Repair of Cisplatin-Induced DNA Damage in Human Ovarian Cancer Cells," Anticancer Res., Mar.-Apr.; 20(2A): 645-52 (2000).

Link, et al., "Thymidylate Synthase Quantitation and in vitro Chemosensitivity Testing Predicts Responses and Survival of Patients with Isolated Nonresectable Liver Tumors Receiving Hepatic Arterial Infusion Chemotherapy," Cancer, Jul. 15; 89(2): 288-96 (2000).

Longley, et al., "Characterization of a Thymidylate Synthase (TS)-Inducible Cell Line: a Model System for Studying Sensitivity to TS- and Non-TS- Targeted Chemotherapies," Clinical Cancer Research, vol. 7, pp. 3533-3539 (2001).

Macfarlane, D. E., et al., "Introduction to Isolating RNA," in RNA Isolation and Characterization Protocols, R. Rapley and D. L. Manning, eds., Humana Press (Series: Methods in Molecular Biology™), Totowa, N. J., pp. 1-6 (1998).

Marsh, S., et al., "Ethnic Variation in the Thymidylate Synthase Enhancer Region Polymorphism among Caucasian and Asian Populations," Genomics, vol. 58, pp. 310-312 (1999).

Metzger R, et al., "ERCC1 mRNA Levels Complement Thymidylate Synthase mRNA Levels in Predicting Response and Survival for Gastric Cancer Patients Receiving Combination Cisplatin and Fluorouracil Chemotherapy," J Clin Oncol 16: 309-316 (1998).

Mies, "A Simple, Rapid Method for Isolating RNA from Paraffin-embedded Tissues for Reverse Transcription-Polymerase Chain Reaction (RT-PCR)," J. Histochemistry and Cytochemistry, vol. 42, No. 6, pp. 811-813 (1994).

Mirjolet, et al., "Thymidylate Synthase Expression and Activity: Relation to S-phase Parameters and 5-fluorouracil Sensitivity," Br J Cancer., Jul.; 78(1): 62-8 (1998).

Miyauchi, et al,"Further Study of Hepatitis C Virus RNA Detection in Formalin-Fixed, Paraffin-Embedded Liver Tissues by Ligation—Dependent Polymerase Chain Reaction," Pathology International: 48: 428-432 (1998).

Mizuno, et al., "RNA from Decades-Old Archival Tissue Blocks for Retrospective Studies," Diagnostic Molecular Pathology, vol. 7, No. 4, pp. 202-208 (1998).

Mukhopadhyay, T., et al., "Isolation of Total RNA from Tissues or Cell Lines," in RNA Isolation and Characterization Protocols, R. Rapley and D. L. Manning, eds., Humana Press (Series: Methods in Molecular Biology™), Totowa, N.J., pp. 55-59 (1998).

Neskovic-Konstantinovic, Z., et al., "Expression of Epidermal Growth Factor Receptor in Breast Cancer, from Early Stages to Advanced Disease," J. Exp. Clin. Cancer Res., 18(3):347-355 (1999).

Newby J.C., et al., "Expression of Epidermal Growth Factor Receptor and c-erbB2 during the Development of Tamoxifen Resistance in Human Breast Cancer," Clinical Cancer Research, 3:1643-1651 (1997).

Nicholson, R.I., et al., "Relationship Between EGF-R, c-erbB-2 Protein Expression and Ki67 Immunostaining in Breast Cancer and Hormone Sensitivity," Eur. J. Cancer, 29A(7):1018-1023 (1993).

Nita, et al., "Dihydropyrimidine Dehydrogenase but not Thymidylate Synthase Expression is Associated with Eesistance to 5-fluorouracil in Colorectal Cancer," Hepatogastroenterology, Nov.-Dec.; 45(24): 2117-22 (1998).

Omura, et al., "Quantification of Thymidylate Synthase Gene Expression in Human Gastrointestinal Carcinoma Tissues Using Competitive PCR," Hepato-Gastroenterology 46(26): pp. 985-990 (1999).

Paradiso, et al., "Thymidilate Synthase and p53 Primary Tumor Expression as Predictive Factors for Advanced Colorectal Cancer Patients," British Journal of Cancer 82(3): pp. 560-567 (2000).

Park, Y. N., et al., "Detection of Hepatitis C Virus RNA Using Ligation-Dependent Polymerase Chain Reaction in Formalin-Fixed, Paraffin-Embedded Liver Tissues," American Journal of Pathology, vol. 149, No. 5, pp. 1485-1491 (1996).

Pestalozzi, et al., "Prognostic Importance of Thymidylate Synthase Expression in Early Breast Cancer," Journal of Clinical Oncology 15(5): pp. 1923-1931 (1997).

Rupp, G. M., et al., "Purification and Analysis of RNA from Paraffin-Embedded Tissues," BioTechniques, vol. 6, No. 1, pp. 56-60 (1988).

(56) References Cited

OTHER PUBLICATIONS

Salonga, et al., "*Colorectal Tumors Responding to 5-fluorouracil Have Low Gene Expression Levels of Dihydropyrirnidine Dehydrogenase, Thymidylate Synthase, and Thymidine Phosphorylase*," Clin Cancer Res., Apr.; 6(4): 1322-7 (2000).
Sambrook, J., et al., "*Isolation of High-Molecular-Weight DNA from Mammalian Cells*," in Molecular Cloning: A Laboratory Manual, 2$^{nd}$ Ed., Cold Spring Harbor Laboratory Press, pp. 9.14-9.23 (1989).
Sander, C. A., et al., "*p53 Mutation is Associated with Progression in Follicular Lymphomas*," Blood, vol. 82, No. 7, pp. 1994-2004 (1993).
Santos, A. C., el al., "*Simultaneous Extraction of RNA and DNA from Paraffin-Embedded Tissues*," Trends in Genetics, vol. 9, No. 7, p. 231 (1993).
Schena, et al., "*Quantitative Monitoring of Gene Expression Patterns With a Complementary DNA Microarray*," Science, vol. 270: 467-470 (1995).
Shirota, et al., "*ERCC1 and Thymidylate Synthase mRNA Levels Predict Survivial for Colorectal Cancer Patients Receiving Combination Oxaliplatin and Fluorouracil Chemotherapy*," J Clinical Oncology 19(23): pp. 4298-4304 (2001).
Soguero, C., et al., "*Detection of Hepatitis C Virus RNA in More Than 20-Year Old Paraffin-Embedded Liver Tissue*," Laboratory Investigation, vol. 79, No. 3, pp. 365-366 (1999).
Sorg, I., et al., "*Detection of Borna Disease Virus RNA in Formalin-Fixed, Paraffin-Embedded Brain Tissues by Nested PCR*," J. Clinical Microbiology, vol. 33, No. 4, pp. 821-823 (1995).
Spears, C. P., et al., "*In Vivo Kinetics of Thymidylate Synthetase Inhibition in 5-Fluorouracil-Sensitive and -Resistant Murine Colon Adenocarcinomas*," Cancer Research, vol. 42, pp. 450-456 (1982).
Specht, et al., "*Quantitative Gene Expression Analysis in Microdissected Archival Formalin-Fixed and Paraffin-Embedded Tumor Tissue*," Am J Pathol., Feb.;158(2): 419-2 (2001).
Stanta, et al., "*RNA Extracted from Paraffin-Embedded Human Tissues is Amenable to Analysis by PCR Amplification*," BioTechniques, vol. 11, No. 3, pp. 304-308 (3 pages) (1991).
Stanta, et al., "*RNA Quantitative Analysis from Fixed and Paraffin-Embedded Tissues*," Methods in Molecular Biology, vol. 86, pp. 113-119 (1998).
Stanta, et al., "*RNA Extraction from Formalin-Fixed and Paraffin-Embedded Tissues*," Methods of Molecular Biology, vol. 86, pp. 23-26 (1998).
Sun, et al., Br J Haematol 122(4): 590-599 (2003).
Swain, S. M., et al., "*Fluorouracil and High-Dose Leucovorin in Previously Treated Patients with Metastatic Breast Cancer*," J. Clinical Oncology, vol. 7, No. 7, pp. 890-899 (1989).
Taverna, et al., "*Gene Expression in X-irradiated Human Tumour Cell Lines Expressing Cisplatin Resistance and Altered DNA Repair Capacity*," Carcinogenesis., Sep.;15(9): 2053-6 (1994).
Tomiak, et al., "*Thymidylate Synthase Expression in Stage II and III Colon Cancer*," American Journal of Clinical Onoclogy 24(6): pp. 597-602 (2001).
Van Triest, et al., "*Thymidylate Synthase Expression in Patients with Colorectal Carcinoma Using a Polyclonal Thymidylate Synthase Antibody in Comparison to the TS 106 Monoclonal Antibody*," Journal of Histochemistry & Cytochemistry 48(6): pp. 755-760 (2000).
Wei, X., et al., "*Molecular Basis of the Human Dihydropyrimidine Dehydrogenase Deficiency and 5-Fluorouracil Toxicity*," J. Clinical Investigation, vol. 98, No. 3, pp. 610-615 (1996).
von Weizsäcker, F., et al., "*A Simple and Rapid Method for the Detection of RNA in Formalin-Fixed, Paraffin-Embedded Tissues by PCR Amplification*," Biochem. and Biophys. Research Comm., vol. 174, No. 1, pp. 176-180 (1991).
Wong, Nacs, et al., "*Nuclear thymidylate synthase expression, p53 expression and 5FU response in colorectal carcinoma*," British Journal of Cancer, 85(12):1937-1943 (2001).
Yamada, H., et al., "*Thymidylate Synthase Gene Expression in Primary Colorectal Cancer and Metastatic Sites*," Clinical Colorectal Cancer, 1(3):169-173 (2001); discussion p. 174.
Zhao, et al., "*High-Density cDNA Filter Analysis: A Novel Approach for Large-Scale, Quantitative Analysis of Gene Expression*," Gene, vol. 156: 207-213 (1995).
Nishiyama, et al., "*Low-dose cisplatin and 5-fluorouracil in combination can repress increased gene expression in cellular resistance determinants to themselves*," Clin. Can. Res. 5(9): 2620-2628 (1999).
Sepp, et al., "*Rapid techniques for DNA extraction from routinely processed archival tissue for use in PCR*," J. Clin. Pathol. 47: 318-323 (1994).
Shibata, et al., "*Detection of human papilloma virus in paraffin-embedded tissue using the polymerase chain reaction*," J. Exp. Med. 167: 225-230 (1988).
Tsujitani, et al., "*Expression of thymidylate synthase in relation to survival and chemosensitivity in gastric cancer patients*," J. Exp. Clin. Can. Res. 19(2): 189-195 (2000).

\* cited by examiner

Figure 4  Analysis of Survival of Patients with Colorectal Cancer: Association with TS and ERCC1 mRNA expression (univariate analysis)

| Factor | No. Pts. | Relative Risk[1] | Probability of Survival at 6 Months | p-value[2] |
|---|---|---|---|---|
| TS-Expression |  |  |  | <0.001 |
| Low (≤ 7.5) | 43 | 1.00 | 0.77 ± 0.07 |  |
| High (>7.5) | 7 | 8.44 (2.63,27.13)[3] | 0.00 ± 0.00 |  |
| ERCC1-Expression |  |  |  | <0.001 |
| Low (≤ 4.9) | 40 | 1.00 | 0.76 ± 0.07 |  |
| High (> 4.9) | 10 | 5.76 (2.09,15.88)[3] | 0.16 ± 0.14 |  |
| TS and ERCC1 Expression |  |  |  | <0.001 |
| TS and ERCC1 Low | 36 | 1.00 | 0.85 ± 0.06 |  |
| Others | 14 | 7.12 (2.60,19.52)[3] | 0.10 ± 0.10 |  |

1. Relative risk can be thought as the average increased chance of dying at any point in the time for patients in the second group compared to those in the first group. The group with better prognosis is listed first.
2. Based on logrank test statistics, but after 1,000 bootstrap simulation to adjust for selection of optimal cut-point.
3. 95% confidence interval Figure 5  Analysis of survival of Patients with colorectal cancer: correlation with TS and ERCC1 mRNA expression (stratified analysis)

| Expression | Stratified by | Relative risk[1] | 95% CI[2] | Adjusted p-value[3] |
|---|---|---|---|---|
| TS | ERCC1 | | | 0.002 |
| Low | | 1.00 | | |
| High | | 5.38 | (1.46, 19.92) | |
| ERCC1 | TS | | | 0.008 |
| Low | | 1.00 | | |
| High | | 4.24 | (1.35, 13.29) | |

1. Relative risk can be thought as the average increased chance of dying at any point in time for patients in the second group compared to those in the first group. The group with better prognosis is listed first.
2. 95% confidence interval
3. Based on logrank test statistic, but after 1,000 bootstrap simulation to adjust for selection of optimal cut point.

Figure 7 CHART ILLUSTRATING HOW TO CALCULATE *ERCC1* EXPRESSION RELATIVE TO AN INTERNAL CONTROL GENE

| | Sample | from "test" reactions | | | | from "calibration" reactions | | | | Uncorrected Gene Expression (UGE) $2^{-\Delta C_T}/2^{-\Delta C_T}$ | Known *ERCC1* values | Derivation of $K_{ERCC1}$ (average K) | | Relative Corrected *ERCC1* exp. |
|---|---|---|---|---|---|---|---|---|---|---|---|---|---|---|
| | | $C_T$ *ERCC1* | $C_T$ β-actin | $\Delta C_T$ | $2^{-\Delta C_T}$ | $C_T$ Calib.RNA | $C_T$ β-actin | $\Delta C_T$ | $2^{-\Delta C_T}$ | | | K | $K_{ERCC1}$ | |
| Experimental | unknown1 | 26.68 | 21.17 | 7.51 | 0.00549 | – | – | – | – | 0.737 | – | | 1.54 x10$^{-3}$ | 1.13 x 10$^{-3}$ |
| | unknown2 | 24.8 | 17.64 | 7.16 | 0.00699 | – | – | – | – | 0.9395 | – | | 1.54 x10$^{-3}$ | 1.45 x 10$^{-3}$ |
| | Calib. RNA | – | – | – | – | 27.81 | 20.71 | 7.07 | 0.0074 | 0.0074/0.0074 = 1 | | | | |
| From Known Samples | AG221 | 34.46 | 28.56 | 5.9 | 0.167 | – | – | – | – | 2.81 | 4.32 x 10$^{-3}$ | 1.54 x10$^{-3}$ | 1.54 x10$^{-3}$ | – |
| | AG222 | 33.93 | 27.21 | 6.72 | 0.0095 | – | – | – | – | 1.59 | 2.45 x 10$^{-3}$ | 1.54 x10$^{-3}$ | 1.54 x10$^{-3}$ | – |
| | AG252 | 36.9 | 29.43 | 7.47 | 0.0056 | – | – | – | – | 0.946 | 1.46 x 10$^{-3}$ | 1.54 x10$^{-3}$ | 1.54 x10$^{-3}$ | – |
| | Adult Lung | 25.2 | 17.3 | 8 | 0.0039 | – | – | – | – | 0.655 | 1.009 x 10$^{-3}$ | 1.54 x10$^{-3}$ | 1.54 x10$^{-3}$ | – |
| | PC3 | 24.51 | 16.47 | 8.04 | 0.0038 | – | – | – | – | 0.637 | 0.981 x 10$^{-3}$ | 1.54 x10$^{-3}$ | 1.54 x10$^{-3}$ | – |
| | AdCol | 24.46 | 16.75 | 7.71 | 0.0048 | – | – | – | – | 0.801 | 1.233 x 10$^{-3}$ | 1.54 x10$^{-3}$ | 1.54 x10$^{-3}$ | – |
| | Calib. RNA | – | – | – | – | 25.96 | 18.57 | 7.39 | 0.00596 | 0.00596/0.00596 = 1 | – | – | – | – |

| | | From "Test" Reactions | | | From "Calibration" Reactions | | | | Uncorrected Gene Expression (UGE) | Published TS Values | Derivation of $K_{TS}$ (Avg. K) | | Corrected Relative TS. exp. |
|---|---|---|---|---|---|---|---|---|---|---|---|---|---|
| | Sample | $C_T$ TS | $C_T$ β-ACTIN | $\Delta C_T$ | $2^{-\Delta C_T}$ | $C_T$ calib. RNA | $C_T$ β-ACTIN | $\Delta C_T$ | $2^{-\Delta C_T}$ | $2^{-\Delta C_T}/2^{-\Delta C_T}$ | | K | $K_{TS}$ | |
| Experimental | Unknown 1 | 26.14 | 19.35 | 6.79 | 0.00903 | – | – | – | – | 0.178 | – | | | 2.25 × $10^{-3}$ |
| | Unknown 2 | 32.07 | 28.38 | 3.69 | 0.0748 | – | – | – | – | 1.33 | – | | | 16.758 × $10^{-3}$ |
| | Calib. RNA | – | – | – | – | 27.94 | 23.79 | 4.15 | 0.0563 | 0.056/0.056 = 1 | | | | |
| From Published Data | L7 | 26.94 | 24.55 | 2.39 | 0.191 | – | – | – | – | 3.18 | 38.8 × $10^{-3}$ | 12.2 × $10^{-3}$ | 12.6 × $10^{-3}$ | – |
| | L91 | 24.91 | 22.12 | 2.79 | 0.144 | – | – | – | – | 2.40 | 29.55 × $10^{-3}$ | 12.31 × $10^{-3}$ | 12.6 × $10^{-3}$ | – |
| | L121 | 24.95 | 20.89 | 4.06 | 0.059 | – | – | – | – | 0.88 | 12.22 × $10^{-3}$ | 13.88 × $10^{-3}$ | 12.6 × $10^{-3}$ | – |
| | L150 | 29.77 | 22.88 | 6.89 | 0.008 | – | – | – | – | 0.133 | 1.72 × $10^{-3}$ | 12.93 × $10^{-3}$ | 12.6 × $10^{-3}$ | – |
| | L220 | 26.52 | 19.77 | 6.75 | 0.0092 | – | – | – | – | 0.153 | 1.89 × $10^{-3}$ | 12.35 × $10^{-3}$ | 12.6 × $10^{-3}$ | – |
| | L164 | 26.81 | 21.21 | 5.6 | 0.0205 | – | – | – | – | 0.341 | 4.2 × $10^{-3}$ | 12.31 × $10^{-3}$ | 12.6 × $10^{-3}$ | – |
| | Calib. RNA | – | – | – | – | 25.14 | 20.09 | 5.04 | 0.06 | 0.06/0.06 = 1 | – | – | – | – |

Figure 8 CHART ILLUSTRATING HOW TO CALCULATE TS EXPRESSION RELATIVE TO AN INTERNAL CONTROL GENE

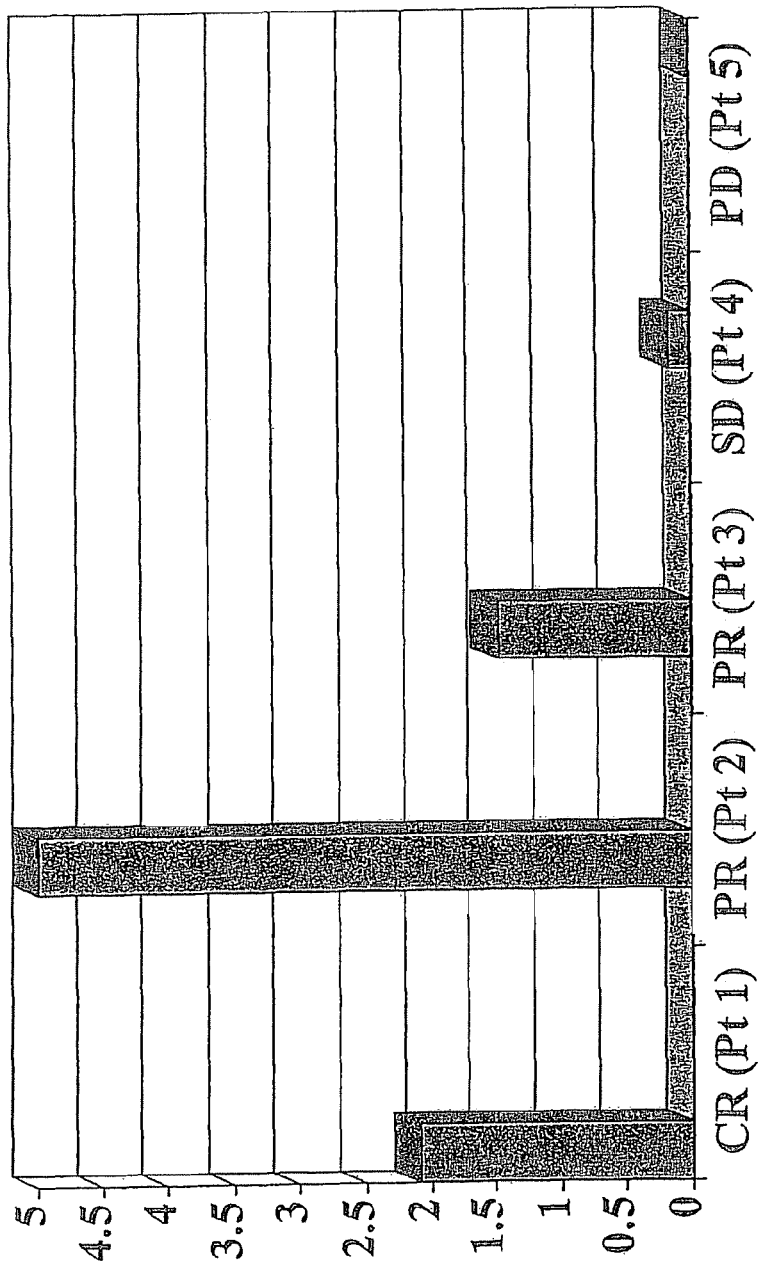

METHOD OF DETERMINING A CHEMOTHERAPEUTIC REGIMEN BASED ON ERCC1 AND TS EXPRESSION

This application is a continuation of U.S. application Ser. No. 12/502,753, filed Jul. 14, 2009, now U.S. Pat. No. 7,732,144 which is continuation of U.S. application Ser. No. 11/341,515, filed Jan. 30, 2006, now U.S. Pat. No. 7,560,543, issued Jul. 14, 2009, which is a divisional application of U.S. application Ser. No. 09/877,178, filed Jun. 11, 2001, now U.S. Pat. No. 7,049,059, issued May 23, 2006, which claims the benefit of U.S. Provisional Application Nos. 60/250,358, filed Dec. 1, 2000, and 60/250,471, filed Dec. 4, 2000, the entire contents of which are hereby incorporated by reference into this application.

FIELD OF THE INVENTION

The present invention relates to prognostic methods which are useful in medicine, particularly cancer chemotherapy. More particularly, the invention relates to assessment of tumor cell gene expression in a patient. The resistance of tumor cells to cytotoxic chemotherapeutic agents, especially antimetabolites and agents that damage DNA in the manner of platinating agents is assayed by examining the mRNA expressed from genes involved in nucleotide synthesis and DNA repair in humans.

BACKGROUND OF THE INVENTION

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor. When a tumor is found, the clinical objective is to destroy malignant cells selectively while mitigating any harm caused to normal cells in the individual undergoing treatment.

Chemotherapy is based on the use of drugs that are selectively toxic (cytotoxic) to cancer cells. Several general classes of chemotherapeutic drugs have been developed, including drugs that interfere with nucleic acid synthesis, protein synthesis, and other vital metabolic processes. These generally are referred to as antimetabolite drugs. Other classes of chemotherapeutic drugs inflict damage on cellular DNA. Drugs of these classes generally are referred to as genotoxic.

Susceptibility of an individual neoplasm to a desired chemotherapeutic drug or combination of drugs often, however, can be accurately assessed only after a trial period of treatment. The time invested in an unsuccessful trial period poses a significant risk in the clinical management of aggressive malignancies.

The repair of damage to cellular DNA is an important biological process carried out by a cell's enzymatic DNA repair machinery. Unrepaired lesions in a cell's genome can impede DNA replication, impair the replication fidelity of newly synthesized DNA and/or hinder the expression of genes needed for cell survival. Thus, genotoxic drugs generally are considered more toxic to actively dividing cells that engage in DNA synthesis than to quiescent, nondividing cells. Normal cells of many body tissues, however, are quiescent and commit infrequently to re-enter the cell cycle and divide. Greater time between rounds of cell division generally is afforded for the repair of DNA damage in normal cells inflicted by chemotherapeutic genotoxins. As a result, some selectivity is achieved for the killing of cancer cells. Many treatment regimes reflect attempts to improve selectivity for cancer cells by coadministering chemotherapeutic drugs belonging to two or more of these general classes.

Because effective chemotherapy in solid tumors often requires a combination of agents, the identification and quantification of determinants of resistance or sensitivity to each single drug has become an important tool to design individual combination chemotherapy.

Widely used genotoxic anticancer drugs that have been shown to damage cellular DNA are cisplatin (DDP) and carboplatin. Cisplatin and/or carboplatin currently are used in the treatment of selected, diverse neoplasms of epithelial and mesenchymal origin, including carcinomas and sarcomas of the respiratory, gastrointestinal and reproductive tracts, of the central nervous system, and of squamous origin in the head and neck. Cisplatin in combination with other agents is currently preferred for the management of testicular carcinoma, and in many instances produces a lasting remission. (Loehrer et al., 1984, 100 Ann. Int. Med. 704). Cisplatin (DDP) disrupts DNA structure through formation of intrastrand adducts. Resistance to platinum agents such as DDP has been attributed to enhanced tolerance to platinum adducts, decreased drug accumulation, or enhanced DNA repair.

Oxaliplatin, another platinum-based chemotherapeutic agent carrying a 1,2-diaminocyclohexane ring has shown anti-tumor efficacy in vitro and in vivo. This bulky carrier group is considered to lead to platinum-DNA adducts, which are more cytotoxic than adducts formed from other platinum agents and more effective at blocking DNA replication. Recent data have shown that deficiency in the mismatch repair system (MMR) as well as increased ability of the replication complex to synthesize DNA past the site of DNA damage (enhanced replicative bypass) cause resistance to cisplatin, but not to oxaliplatin (Raymond et al., Semin Oncol 25, Suppl 5: 4-12, 1998).

Excision repair of bulky DNA adducts, such as those formed by platinum agents, appears to be mediated by genes involved in DNA damage recognition and excision. Cleaver et al., Carcinogenesis 11:875-882 (1990); Hoeijmakers et al., Cancer Cells 2:311-320 (1990); Shivji et al., Cell 69:367-374 (1992). Indeed, cells carrying a genetic defect in one or more elements of the enzymatic DNA repair machinery are extremely sensitive to cisplatin. Fraval et al. (1978), 51 Mutat. Res. 121, Beck and Brubaker (1973), 116 J. Bacteriol 1247.

The excision repair cross-complementing (ERCC1) gene is essential in the repair of DNA adducts. The human ERCC1 gene has been cloned. Westerveld et al., Nature (London) 310:425-428 (1984); Tanaka et al., Nature 348:73-76 (1990); (Accession No. XM_009432, incorporated by reference herein with SEQ ID NO: 10). Several studies using mutant human and hamster cell lines that are defective in this gene and studies in human tumor tissues indicate that the product encoded by ERCC1 is involved in the excision repair of platinum-DNA adducts. Dabholkar et al., J. Natl. Cancer Inst. 84:1512-1517 (1992); Dijt et al., Cancer Res. 48:6058-6062 (1988); Hansson et al., Nucleic Acids Res. 18: 35-40 (1990).

When transfected into DNA-repair deficient CHO cells, ERCC1 confers cellular resistance to platinum-based chemotherapy by its ability to repair platinum-DNA adducts. Hansson et al., Nucleic Acids Res. 18: 35-40 (1990). Currently accepted models of excision repair suggest that the damage recognition/excision step is rate-limiting to the excision repair process.

The relative levels of expression of excision repair genes such as ERCC1 in malignant cells from cancer patients receiving platinum-based therapy has been examined. Dabholkar et al., J. Natl. Cancer Inst. 84:1512-1517 (1992).

ERCC1 overexpression in gastric cancer patients has been reported to have a negative impact on tumor response and ultimate survival when treated with the combined platinum-based and antimetabolite-based chemotherapeutic regimen (cisplatin/fluorouracil), (Metzger, et al., J Clin Oncol 16: 309, 1998). Thus, intratumoral levels of ERCC1 expression may be a major prognostic factor for determining whether or not a platinum-based chemotherapy either alone or combined with an antimetabolite-based therapy would be effective in treating cancer patients.

Antimetabolic cytotoxic chemotherapeutic compounds include drugs that interfere with nucleic acid synthesis, protein synthesis, and other vital metabolic processes. For example, 5-Fluorouracil (5-FU) is a very widely used drug used for the treatment of many different types of cancers, including major cancers such as those of the GI tract and breast (Moertel, C. G. New Engl. J. Med., 330:1136-1142, 1994). 5-FU as a single agent was for more than 40 years the standard first-line treatment for colorectal cancer, but the combination of 5-FU and CPT-11 has recently been introduced as an alternative first-line therapy for advanced colorectal cancer (Saltz et al., Irinotecan Study Group. New England Journal of Medicine. 343:905-14, 2000). The combination of 5-FU and oxaliplatin has produced high response rates in colorectal cancers (Raymond et al., Semin. Oncol., 25:4-12, 1998). Thus, it is likely that 5-FU will be used in cancer treatment for many years because it remains the central component of current chemotherapeutic regimens. In addition, single agent 5-FU therapy continues to be used for patients in whom combination therapy with CPT-11 or oxaliplatin is likely to be excessively toxic.

5-FU is typical of most anti-cancer drugs in that only the minority of patients experience a favorable response to the therapy. Large randomized clinical trials have shown the overall response rates of tumors to 5-FU as a single agent for patients with metastatic colorectal cancer to be in the 15-20% range (Moertel, C. G. New Engl. J. Med., 330:1136-1142, 1994). In combination with other the chemotherapeutics mentioned above, tumor response rates to 5-FU-based regimens have been increased to almost 40%. Nevertheless, the majority of treated patients derive no tangible benefit from having received 5-FU based chemotherapy, and are subjected to significant risk, discomfort, and expense. Since there has been no reliable means of anticipating the responsiveness of an individual's tumor prior to treatment, the standard clinical practice has been to subject all patients to 5-FU-based treatments, fully recognizing that the majority will suffer an unsatisfactory outcome.

The mechanism of action and the metabolic pathway of 5-FU have been intensively studied over the years to identify the most important biochemical determinants of the drug's anti-tumor activity. The ultimate goal was to improve the clinical efficacy of 5-FU by a) modulation of its intracellular metabolism and biochemistry and b) by measuring response determinants in patients' tumors prior to therapy to predict which patients are most likely to respond (or not to respond) to the drug.

The first studies in the area of tumor response prediction to 5-FU based therapy centered on its target enzyme, Thymidylate Synthase (TS), in colorectal cancer. TS has also been cloned. (Kaneda et al., J. Biol. Chem. 265 (33), 20277-20284 (1990); Accession No. NM_001071, incorporated by reference herein with SEQ ID NO: 11). Leichman et al (Leichman et al., J. Clin Oncol., 15:3223-3229, 1997) carried out a prospective clinical trial to correlate tumor response to 5-FU with TS gene expression as determined by RT-PCR in pre-treatment biopsies from colorectal cancers. This study showed: 1) a large 50-fold range of TS gene expression levels among these tumors, and 2) strikingly different levels of TS gene expression between responding and non-responding tumors. The range of TS levels of the responding groups (0.5–4.1× $10^{-3}$, relative to an internal control) was narrower than that of the non-responding groups (1.6–23.0×$10^{-3}$, relative to an internal control). The investigators determined a resulting "non-response cutoff" threshold level of TS expression above which there were only non-responders. Thus, patients with TS expression above this "non-response cutoff" threshold could be positively identified as non-responders prior to therapy. The "no response" classification included all therapeutic responses with <50% tumor shrinkage, progressing growth resulting in a >25% tumor increase and non-progressing tumors with either <50% shrinkage, no change or <25% increase. These tumors had the highest TS levels. Thus, high TS expression identifies especially resistant tumors. TS expression levels above a certain threshold identified a subset of tumors not responding to 5-FU; whereas TS expression levels below this number predicted an appreciably higher response rate.

Interestingly, Papamichael et al., has concluded that oxaliplatin enhances the anabolic pathway for 5-FU in combination treatment. Br. J. Cancer, 78 (Suppl. 2), 98 p. 12, 1998; Oncologist 1999; 4(6):478-87. This may underpin the efficacy of 5-FU and oxaliplatin combination chemotherapy treatment in cancer. Moreover, because 5-FU-based and platinum-based chemotherapy are known to be dependant on TS and ERCC1 expression levels, respectively, it is particularly important to make an accurate determination of ERCC1 expression and TS expression from patient derived tumor tissue samples to prognosticate a 5-FU-based and platinum-based chemotherapy.

Most patient derived pathological samples are routinely fixed and paraffin-embedded (FPE) to allow for histological analysis and subsequent archival storage. Thus, most biopsy tissue samples are not useful for analysis of gene expression because such studies require a high integrity of RNA so that an accurate measure of gene expression can be made. Currently, gene expression levels can be only qualitatively monitored in such fixed and embedded samples by using immunohistochemical staining to monitor protein expression levels.

Until now, quantitative gene expression studies including those of ERCC1 and TS expression have been limited to reverse transcriptase polymerase chain reaction (RT-PCR) amplification of RNA from fresh or frozen tissue. U.S. Pat. No. 5,705,336 to Reed et al., discloses a method of quantifying ERCC1 mRNA from ovarian tumor tissue and determining whether that tissue will be sensitive to platinum-based chemotherapy. As in Leichman et al., Reed et al., quanitfy mRNA from frozen tumor biopsies.

The use of frozen tissue by health care professionals as described in Leichman et al., and Reed et al., poses substantial inconveniences. Rapid biopsy delivery to avoid tissue and subsequent mRNA degradation is the primary concern when planning any RNA-based quantitative genetic marker assay. The health care professional performing the biopsy, must hastily deliver the tissue sample to a facility equipped to perform an RNA extraction protocol immediately upon tissue sample receipt. If no such facility is available, the clinician must promptly freeze the sample in order to prevent mRNA degradation. In order for the diagnostic facility to perform a useful RNA extraction protocol prior to tissue and RNA degradation, the tissue sample must remain frozen until it reaches the diagnostic facility, however far away that may be. Maintaining frozen tissue integrity during transport using specialized couriers equipped with liquid nitrogen and dry ice, comes only at a great expense.

Routine biopsies generally comprise a heterogenous mix of stromal and tumorous tissue. Unlike with fresh or frozen tissue, FPE biopsy tissue samples are readily microdissected and separated into stromal and tumor tissue and therefore, offer advantage over the use of fresh or frozen tissue. However, isolation of RNA from fixed tissue, and especially fixed and paraffin embedded tissue, results in highly degraded RNA, which is generally not thought to be applicable to gene expression studies.

A number of techniques exist for the purification of RNA from biological samples, but none is reliable for isolation of RNA from FPE samples. For example, Chomczynski (U.S. Pat. No. 5,346,994) describes a method for purifying RNA from tissues based on a liquid phase separation using phenol and guanidine isothiocyanate. A biological sample is homogenized in an aqueous solution of phenol and guanidine isothiocyanate and the homogenate thereafter mixed with chloroform. Following centrifugation, the homogenate separates into an organic phase, an interphase and an aqueous phase. Proteins are sequestered in the organic phase, DNA in the interphase, and RNA in the aqueous phase. RNA can be precipitated from the aqueous phase. Unfortunately, this method is not applicable to fixed and paraffin-embedded (FPE) tissue samples.

Other known techniques for isolating RNA typically utilize either guanidine salts or phenol extraction, as described for example in Sambrook, J. et al., (1989) at pp. 7.3-7.24, and in Ausubel, F. M. et al, (1994) at pp. 4.0.3-4.4.7. Again, none of the known methods provides reproducible quantitative results in the isolation of RNA from paraffin-embedded tissue samples.

Techniques for the isolation of RNA from paraffin-embedded tissues are thus particularly needed for the study of gene expression in tumor tissues, since expression levels of certain receptors or enzymes can be used to determine the likelihood of success of a particular treatment.

Molecular predictive markers for resistance or sensitivity of oxaliplatin have not yet been determined. There is a need for such markers to determine the likelihood of success of oxaliplatin/5-FU based therapies. We report here a significant inverse association for both the intratumoral mRNA expression of the excision repair gene ERCC1 and intratumoral mRNA expression of the thymidylate synthase gene (TS) with clinical outcome in patients with tumors undergoing 5-FU/oxaliplatin combination-chemotherapy.

Accordingly, it is the object of the invention to provide a method of quantifying ERCC1 and/or TS mRNA from tumor tissue in order to provide an early prognosis for proposed genotoxic cancer therapies. It is also the object of the invention to provide a method for assessing ERCC1 and/or TS levels in tissues fixed and paraffin-embedded (FPE) and predicting the probable resistance of a patient's tumor to treatment with 5-FU and oxaliplatin by examining the amount ERCC1 and/or TS mRNA in a patient's tumor cells and comparing it to a predetermined threshold expression level.

SUMMARY OF THE INVENTION

In one aspect of the invention there is provided a method for assessing levels of expression of ERCC1 mRNA obtained from fixed or fixed and paraffin-embedded (FPE) tumor cells.

In another aspect of the invention there is provided a method for assessing levels of expression of TS mRNA obtained from fixed or fixed and paraffin-embedded (FPE) tumor cells.

In another aspect of the invention there is provided a method of quantifying the amount of ERCC1 mRNA expression relative to an internal control from a fixed and paraffin-embedded (FPE) tissue sample. This method includes isolation of total mRNA from said sample and determining the quantity of ERCC1 mRNA relative to the quantity of an internal control gene's mRNA.

In another aspect of the invention there is provided a method of quantifying the amount of TS mRNA expression relative to an internal control from a fixed and paraffin-embedded (FPE) tissue sample. This method includes isolation of total mRNA from said sample and determining the quantity of TS mRNA relative to the quantity of an internal control gene's mRNA.

In an embodiment of this aspect of the invention, there are provided oligonucleotide primers having the sequence of ERCC1-504F (SEQ ID NO: 1) or ERCC1-5748 (SEQ ID NO:2) and sequences substantially identical thereto. The invention also provides for oligonucleotide primers having a sequence that hybridizes to SEQ ID NO: 1 or SEQ ID NO:2 or their complements under stringent conditions.

In another embodiment of this aspect of the invention, there are provided oligonucleotide primers having the sequence of TS-763F (SEQ ID NO: 3) or TS-825R (SEQ ID NO: 4) and sequences substantially identical thereto. The invention also provides for oligonucleotide primers having a sequence that hybridizes to SEQ ID NO: 3 or SEQ ID NO:4 or their complements under stringent conditions.

In yet another aspect of the invention there is provided a method for determining a 5-FU and oxaliplatin-based chemotherapeutic regimen for a patient, comprising isolating RNA from a fixed and paraffin-embedded (FPE) tumor sample; determining a gene expression level of ERCC1 in the sample; comparing the ERCC1 gene expression levels in the sample with a predetermined threshold level for the ERCC1 gene; and determining a chemotherapeutic regimen based on results of the comparison of the ERCC1 gene expression level with the predetermined threshold level.

In yet another aspect of the invention there is provided a method for determining a 5-FU and oxaliplatin-based chemotherapeutic regimen for a patient, comprising isolating RNA from a fixed and paraffin-embedded (FPE) tumor sample; determining a gene expression level of TS in the sample; comparing the TS gene expression levels in the sample with a predeterimined threshold level for the TS gene; and determining a chemotherapeutic regimen based on results of the comparison of the TS gene expression level with the predetermined threshold level.

In yet another aspect of the invention there is provided a method for determining a 5-FU and oxaliplatin-based chemotherapeutic regimen for a patient, comprising isolating RNA from a fixed and paraffin-embedded (FPE) tumor sample; determining gene expression levels of TS and ERCC1 in the sample; comparing the TS and ERCC1 gene expression levels in the sample with a predetermined threshold level for each of the TS and ERCC1 genes; and determining a chemotherapeutic regimen based on results of the comparison of the TS and ERCC1 gene expression levels with the predetermined threshold levels.

The invention further relates to a method of normalizing the uncorrected gene expression (UGE) of ERCC1 and TS relative to an internal control gene in a tissue sample analyzed using TaqMan® technology to known ERCC1 and TS expression levels relative to an internal control from samples analyzed by pre-TaqMan® technology.

DESCRIPTION OF THE DRAWING

FIG. 4 is a table showing the survival of oxaliplatin/5-FU treated colorectal cancer patients relative to ERCC1 and TS expression analyzed by univariate analysis.

FIG. 5 is a table showing the survival of oxaliplatin/5-FU treated colorectal cancer patients relative to ERCC1 and TS expression analyzed by stratified analysis.

FIG. 7 is a chart illustrating how to calculate ERCC1 expression relative to an internal control gene. The chart contains data obtained with two test samples, (unknowns 1 and 2), and illustrates how to determine the uncorrected gene expression data (UGE). The chart also illustrates how to normalize UGE generated by the TaqMan® instrument with known relative ERCC1 values determined by pre-TaqMan® technology. This is accomplished by multiplying UGE to a correction factor $K_{ERCC1}$. The internal control gene in the figure is β-actin and the calibrator RNA is Human Liver Total RNA (Stratagene, Cat. #735017).

FIG. 8 is a chart illustrating how to calculate TS expression relative to an internal control gene. The chart contains data obtained with two test samples, (unknowns 1 and 2), and illustrates how to determine the uncorrected gene expression data (UGE). The chart also illustrates how to normalize UGE generated by the TaqMan® instrument with previously published TS values. This is accomplished by multiplying UGE to a correction factor $K_{TS}$. The internal control gene in the figure is β-actin and the calibrator RNA is Universal PE RNA; Cat #4307281, lot #3617812014 from Applied Biosystems.

FIG. 9 is a table showing colorectal cancer patients' tumors response to oxaliplatin/5-FU treatmeant relative TS expression.

DETAILED DESCRIPTION OF THE INVENTION

Figure 1:
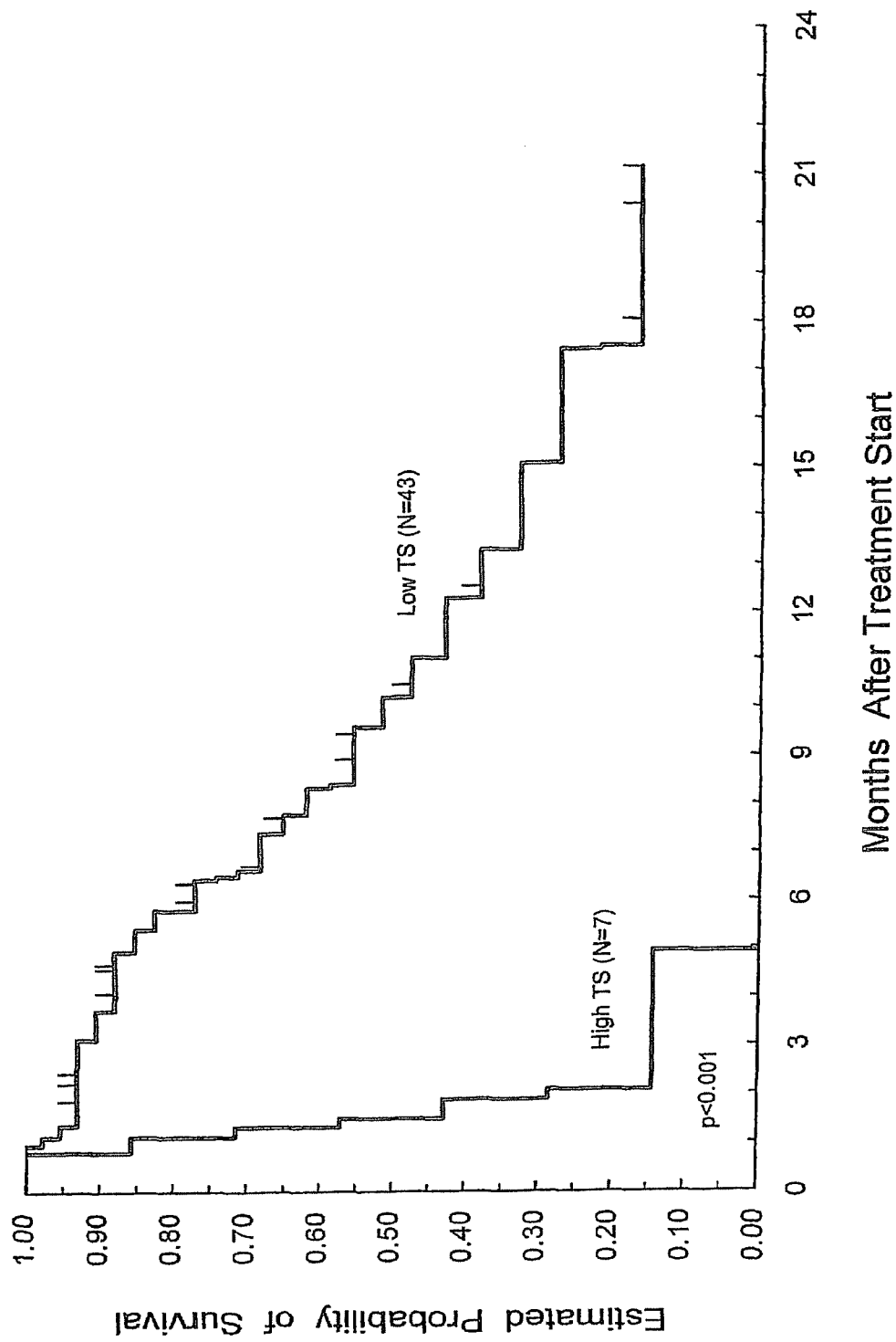
FIG. 1 is a graph showing the estimated probability of survival and survival in months of colorectal adenocarcinoma tumor carrying patients with high (greater than about 7.5× $10^{-3}$ times β-actin gene expression; n=7) and low (less than about 7.5×$10^{-3}$ times β-actin gene expression; n=43) corrected TS expression levels receiving 5-FU and oxaliplatin therapeutic regimen.

The present invention resides in part in the finding that the amount of TS and ERCC1 mRNA is correlated with resistance to 5-FU and oxaliplatin agents, respectively. Tumors expressing high levels of TS and/or ERCC1 mRNA are considered likely to be resistant to platinum-based chemotherapy. Conversely, those tumors expressing low amounts of TS and ERCC1 mRNA are likely to be sensitive to platinum-based chemotherapy. A patient's tumor TS and ERCC1 mRNA expression status is judged by comparing it to a pre-determined threshold expression level.

The invention provides a method of quantifying the amount of TS and/or ERCC1 mRNA expression in fixed or fixed and paraffin-embedded (FPE) tissue relative to gene expression of an internal control. The present inventors have developed oligonucleotide primers that allow accurate assessment of TS and ERCC1 gene expression in tissues that have been fixed or fixed and embedded. The invention oligonucleotide primers, ERCC1-504F (SEQ ID NO: 1), ERCC1-574R (SEQ ID NO: 2), or oligonucleotide primers substantially identical thereto, preferably are used together with RNA extracted from fixed and paraffin embedded (FPE) tumor samples. The invention also provides oligonucleotide primers, TS-763F (SEQ ID NO: 3), TS-825R (SEQ ID NO: 4), or oligonucleotide primers substantially identical thereto, preferably are used together with RNA extracted from fixed and paraffin embedded (FPE) tumor samples. This measurement of TS and/or ERCC1 gene expression may then be used for prognosis of platinum-based chemotherapy This embodiment of the invention involves first, a method for reliable extraction of RNA from an FPE sample and second, determination of the content of ERCC1 mRNA in the sample by using a pair of oligonucleotide primers, preferably oligonucleotide primer pair ERCC1-504F (SEQ ID NO: 1) and ERCC1-574R (SEQ ID NO: 2), or oligonucleotides substantially identical thereto, for carrying out reverse transcriptase polymerase chain reaction.

"Substantially identical" in the nucleic acid context as used herein, means hybridization to a target under stringent conditions, and also that the nucleic acid segments, or their complementary strands, when compared, are the same when properly aligned, with the appropriate nucleotide insertions and deletions, in at least about 60% of the nucleotides, typically, at least about 70%, more typically, at least about 80%, usually, at least about 90%, and more usually, at least, about 95-98% of the nucleotides. Selective hybridization exists when the hybridization is more selective than total lack of specificity. See, Kanehisa, Nucleic Acids Res., 12:203-213 (1984).

This embodiment of the invention further involves first determination of the content of TS mRNA in the sample by using a pair of oligonucleotide primers, preferably oligonucleotide primer pair TS-763F (SEQ ID NO: 3) and TS-825R (SEQ ID NO: 4), or oligonucleotides substantially identical thereto, for carrying out reverse transcriptase polymerase chain reaction. RNA is extracted from the FPE cells by any of the methods for mRNA isolation from such samples as described in U.S. patent application Ser. No. 09/469,338, filed Dec. 20, 1999, and is hereby incorporated by reference in its entirety.

The present method can be applied to any type of tissue from a patient. For examination of resistance of tumor tissue, it is preferable to examine the tumor tissue. In a preferred embodiment, a portion of normal tissue from the patient from which the tumor is obtained, is also examined. Patients whose normal tissues are expected to be resistant to platinum-based chemotherapeutic compounds, i.e., show a high level of TS and/or ERCC1 gene expression, but those whose tumors are expected to be sensitive to such compounds, i.e. show a low level of TS and/or ERCC1 gene expression, may then be treated with higher amounts of the chemotherapeutic composition.

The methods of the present invention can be applied over a wide range of tumor types. This allows for the preparation of individual "tumor expression profiles" whereby expression levels of TS and/or ERCC1 are determined in individual patient samples and response to various chemotherapeutics is predicted. Preferably, the methods of the invention are applied to solid tumors, most preferably colorectal adenocarcinoma tumors.

A "predetermined threshold level", as defined herein relating to ERCC1 expression, is a level of ERCC1 expression above which it has been found that tumors are likely to be resistant to a 5-FU and/or oxaliplatin-based chemotherapeutic regimen. Expression levels below this threshold level are likely to be found in tumors sensitive to 5-FU and/or oxaliplatin-based chemotherapeutic regimen. The range of relative expression of ERCC1, expressed as a ratio of ERCC1:β-actin, among tumors responding to a platinum-based chemotherapeutic regimen is less than about $4.9 \times 10^3$. Tumors that do not respond to a platinum-based chemotherapeutic regimen have relative expression of ERCC1:β-actin ratio above about $4.9 \times 10^{-3}$.

A "predetermined threshold level", as defined herein relating to TS, is a level of TS expression above which it has been found that tumors are likely to be resistant to a 5-FU and 5-FU and oxaliplatin-based chemotherapeutic regimen. Expression levels below this threshold level are likely to be found in tumors sensitive to 5-FU or 5-FU and oxaliplatin-based chemotherapeutic regimen. The range of relative expression of TS, expressed as a ratio of TS:β-actin, among tumors responding to a 5-FU or 5-FU and oxaliplatin-based chemotherapeutic chemotherapeutic regimen is less than about $7.5 \times 10^{-3}$. Tumors that do not respond to a 5-FU or 5-FU and oxaliplatin-based chemotherapeutic regimen have relative expression of TS:β-actin ratio above about $7.5 \times 10^{-3}$.

In performing the method of the present invention either ERCC1 expression levels or TS expression levels are assayed in patient tumor samples to prognosticate the efficacy of a 5-FU and oxaliplatin-based chemotherapeutic regimen. Moreover, in the method of the present invention TS expression levels are assayed in patient tumor samples to prognosticate the efficacy of a 5-FU based chemotherapeutic regimen. Additionally, in the method of the present invention ERCC1 expression levels are assayed in patient tumor samples to prognosticate the efficacy of a oxaliplatin based chemotherapeutic regimen. Alternatively, both ERCC1 expression levels and TS expression levels are assayed in patient tumor samples to prognosticate the efficacy of a combined 5-FU and oxaliplatin-based chemotherapeutic regimen.

In performing the method of this embodiment of the present invention, tumor cells are preferably isolated from the patient. Solid or lymphoid tumors or portions thereof are surgically resected from the patient or obtained by routine biopsy. RNA isolated from frozen or fresh samples is extracted from the cells by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of the RNA during the extraction process.

However, tissue obtained from the patient after biopsy is often fixed, usually by formalin (formaldehyde) or gluteraldehyde, for example, or by alcohol immersion. Fixed biological samples are often dehydrated and embedded in paraffin or other solid supports known to those of skill in the art. See Plenat et al., Ann Pathol 2001 January; 21(1):29-47. Non-embedded, fixed tissue as well as fixed and embedded tissue may also be used in the present methods. Solid supports for embedding fixed tissue are envisioned to be removable with organic solvents for example, allowing for subsequent rehydration of preserved tissue.

RNA is extracted from the FPE cells by any of the methods as described in U.S. patent application Ser. No. 09/469,338, filed Dec. 20, 1999, which is hereby incorporated by reference in its entirety. Fixed and paraffin-embedded (FPE) tissue samples as described herein refers to storable or archival tissue samples. RNA may be isolated from an archival pathological sample or biopsy sample which is first deparaffinized. An exemplary deparaffinization method involves washing the paraffinized sample with an organic solvent, such as xylene, for example. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration, for example. Alternatively, the sample is simultaneously deparaffinized and rehydrated. RNA is then extracted from the sample.

For RNA extraction, the fixed or fixed and deparaffinized samples can be homogenized using mechanical, sonic or other means of homogenization. Rehydrated samples may be homogenized in a solution comprising a chaotropic agent, such as guanidinium thiocyanate (also sold as guanidinium isothiocyanate). Homogenized samples are heated to a temperature in the range of about 50 to about 100° C. in a chaotropic solution, which contains an effective amount of a chaotropic agent, such as a guanidinium compound. A preferred chaotropic agent is guanidinium thiocyanate.

An "effective concentration of chaotropic agent" is chosen such that at an RNA is purified from a paraffin-embedded sample in an amount of greater than about 10-fold that isolated in the absence of a chaotropic agent. Chaotropic agents include, for example: guanidinium compounds, urea, formamide, potassium iodiode, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The effective concentration of guanidinium solution used in the invention generally has a concentration in the range of about 1 to about 5M with a preferred value of about 4M. If RNA is already in solution, the guanidinium solution may be of higher concentration such that the final concentration achieved in the sample is in the range of about 1 to about 5M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT) and β-mercaptoethanol (BME). The chaotropic solution may also contain RNAse inhibitors.

RNA is then recovered from the chaotropic solution by, for example, phenol chloroform extraction, ion exchange chromatography or size-exclusion chromatography. RNA may then be further purified using the techniques of extraction, electrophoresis, chromatography, precipitation or other suitable techniques.

The quantification of TS or ERCC1 mRNA from purified total mRNA from fresh, frozen or fixed is preferably carried out using reverse-transcriptase polymerase chain reaction (RT-PCR) methods common in the art, for example. Other methods of quantifying of TS or ERCC1 mRNA include for example, the use of molecular beacons and other labeled probes useful in multiplex PCR. Additionally, the present invention envisages the quantification of TS and/or ERCC1 mRNA via use of a PCR-free systems employing, for example fluorescent labeled probes similar to those of the Invader® Assay (Third Wave Technologies, Inc.). Most preferably, quantification of TS and/or ERCC1 cDNA and an internal control or house keeping gene (e.g. β-actin) is done using a fluorescence based real-time detection method (ABI PRISM 7700 or 7900 Sequence Detection System [TaqMan®], Applied Biosystems, Foster City, Calif.) or similar system as described by Heid et al., (Genome Res 1996; 6:986-994) and Gibson et al. (Genome Res 1996; 6:995-1001). The output of the ABI 7700 (TaqMan® Instrument) is expressed in Ct's or "cycle thresholds". With the TaqMan® system, a highly expressed gene having a higher number of target molecules in a sample generates a signal with fewer PCR cycles (lower Ct) than a gene of lower relative expression with fewer target molecules (higher Ct).

As used herein, a "house keeping" gene or "internal control" is meant to include any constitutively or globally expressed gene whose presence enables an assessment of TS and/or ERCC1 mRNA levels. Such an assessment comprises a determination of the overall constitutive level of gene transcription and a control for variations in RNA recovery. "House-keeping" genes or "internal controls" can include, but are not limited to the cyclophilin gene, β-actin gene, the transferrin receptor gene, GAPDH gene, and the like. Most preferably, the internal control gene is β-actin gene as described by Eads et al., Cancer Research 1999; 59:2302-2306.

A control for variations in RNA recovery requires the use of "calibrator RNA." The "calibrator RNA" is intended to be any available source of accurately pre-quantified control RNA. Preferably, Human Liver Total RNA (Stratagene, Cat. #735017) is used in quantifying ERCC1 and Universal PE RNA; Cat #4307281, lot #3617812014 from Applied Biosystems is used in quantifying TS.

"Uncorrected Gene Expression (UGE)" as used herein refers to the numeric output of TS and/or ERCC1 expression relative to an internal control gene generated by the TaqMan® instrument. The equation used to determine UGE is shown in Examples 3 and 4, and illustrated with sample calculations in FIGS. 7 and 8.

A further aspect of this invention provides a method to normalize uncorrected gene expression (UGE) values acquired from the TaqMan® instrument with "known relative gene expression" values derived from non-TaqMan® technology. Preferably, TaqMan® derived TS and/or ERCC1 UGE values from a tissue sample are normalized to samples with known non-TaqMan® derived relative TS and/or ERCC1: β-actin expression values.

"Corrected Relative ERCC1 Expression" as used herein refers to normalized ERCC1 expression whereby UGE is multiplied with a ERCC1 specific correction factor ($K_{ERCC1}$), resulting in a value that can be compared to a known range of ERCC1 expression levels relative to an internal control gene. Example 3 and FIG. 7 illustrate these calculations in detail. These numerical values allow the determination of whether or not the "Corrected Relative ERCC1 Expression" of a particular sample falls above or below the "predetermined threshold" level. The predetermined threshold level of Corrected Relative ERCC1 Expression to β-actin level is about $4.9 \times 10^{-3}$. $K_{ERCC1}$ specific for ERCC1, the internal control β-actin and calibrator Human Liver Total RNA (Stratagene, Cat. #735017), is $1.54 \times 10^{-3}$.

"Known relative gene expression" values are derived from previously analyzed tissue samples and are based on the ratio of the RT-PCR signal of a target gene to a constitutively expressed internal control gene (e.g. β-Actin, GAPDH, etc.). Preferably such tissue samples are formalin fixed and paraffin-embedded (FPE) samples and RNA is extracted from them according to the protocol described in Example 1 and in U.S. patent application Ser. No. 09/469,338, filed Dec. 20, 1999, which is hereby incorporated by reference in its entirety. To quantify gene expression relative to an internal control standard quantitative RT-PCR technology known in the art is used. Pre-TaqMan® technology PCR reactions are run for a fixed number of cycles (i.e., 30) and endpoint values are reported for each sample. These values are then reported as a ratio of ERCC1 expression to β-actin expression. See U.S. Pat. No. 5,705,336 to Reed et al.

$K_{ERCC1}$ may be determined for an internal control gene other than β-actin and/or a calibrator RNA different than Human Liver Total RNA (Stratagene, Cat. #735017). To do so, one must calibrate both the internal control gene and the calibrator RNA to tissue samples for which ERCC1 expression levels relative to that particular internal control gene have already been determined (i.e., "known relative gene expression"). Preferably such tissue samples are formalin fixed and paraffin-embedded (FPE) samples and RNA is extracted from them according to the protocol described in Example 1 and in U.S. patent application Ser. No. 09/469,338, filed Dec. 20, 1999, which is hereby incorporated by reference in its entirety. Such a determination can be made using standard pre-TaqMan®, quantitative RT-PCR techniques well known in the art. Upon such a determination, such samples have "known relative gene expression" levels of ERCC1 useful in the determining a new $K_{ERCC1}$ specific for the new internal control and/or calibrator RNA as described in Example 3.

"Corrected Relative TS Expression" as used herein refers to normalized TS expression whereby UGE is multiplied with a TS specific correction factor ($K_{TS}$), resulting in a value that can be compared to a known range of TS expression levels relative to an internal control gene. Example 4 and FIG. 8 illustrate these calculations in detail. These numerical values allow the determination of whether the "Corrected Relative TS Expression" of a particular sample falls above or below the "predetermined threshold" level. The predetermined threshold level of Corrected Relative TS Expression to β-actin level is about $7.5 \times 10^{-3}$. $K_{TS}$ specific for TS, the internal control β-actin and calibrator Universal PE RNA; Cat #4307281, lot #3617812014 from Applied Biosystems, is 12.6×

$K_{TS}$ may be determined for an internal control gene other than β-actin and/or a calibrator RNA different than Universal PE RNA; Cat #4307281, lot #3617812014 from Applied Biosystems. To do so, one must calibrate both the internal control gene and the calibrator RNA to tissue samples for which TS expression levels relative to that particular internal control gene have already been determined (i.e., "known relative gene expression" or "previously published"). Preferably such tissue samples are formalin fixed and paraffin-embedded (FPE) samples and RNA is extracted from them according to the protocol described in Example 1 and in U.S. patent application Ser. No. 09/469,338, filed Dec. 20, 1999, which is hereby incorporated by reference in its entirety. Such a determination can be made using standard pre-TaqMan®, quantitative RT-PCR techniques well known in the art. Upon such a determination, such samples have "known relative gene expression" levels of TS useful in the determining a new $K_{TS}$ specific for the new internal control and/or calibrator RNA as described in Example 4.

"Previously published" relative gene expression results are based on the ratio of the RT-PCR signal of a target gene to a constitutively expressed gene (β-Actin). In pre-TaqMan® technology studies, PCR reactions were run for a fixed number of cycles (i.e., 30) and endpoint values were reported for each sample. These values were then reported as a ratio of ERCC1 or TS expression to β-actin expression. Salonga, et al., Clinical Cancer Research, 6:1322-1327, 2000, incorporated herein by reference in its entirety.

The methods of the invention are applicable to a wide range of tissue and tumor types and so can be used for assessment of clinical treatment of a patient and as a diagnostic or prognostic tool for a range of cancers including breast, head and neck, lung, esophageal, colorectal, and others. In a preferred embodiment, the present methods are applied to prognosis of colorectal adenocarcinoma.

Pre-chemotherapy treatment tumor biopsies are usually available only as fixed paraffin embedded (FPE) tissues, generally containing only a very small amount of heterogeneous tissue. Such FPE samples are readily amenable to microdissection, so that TS and/or ERCC1 gene expression may be determined in tumor tissue uncontaminated with stromal tissue. Additionally, comparisons can be made between stromal and tumor tissue within a biopsy tissue sample, since such samples often contain both types of tissues.

Generally, any oligonucleotide pairs that flank a region of ERCC1 gene, as shown in SEQ ID NO: 10, may be used to carry out the methods of the invention. Primers hybridizing under stringent conditions to a region of the ERCC1 gene for use in the present invention will amplify a product between 20-1000 base pairs, preferably 50-100 base pairs, most preferably less than 100 base pairs.

The invention provides specific oligonucleotide primer pairs and oligonucleotide primers substantially identical thereto, that allow particularly accurate assessment of ERCC1 expression using FPE tissues. Preferable are oligonucleotide primers, ERCC1-504F (SEQ ID NO: 1) and ERCC1 (SEQ ID NO: 2), (also referred to herein as the oligonucleotide primer pair ERCC1) and oligonucleotide primers substantially identical thereto. The oliogonucleotide primers ERCC1-504F (SEQ ID NO: 1) and ERCC1, (SEQ ID NO: 2) have been shown to be particularly effective for measuring ERCC1 mRNA levels using RNA extracted from the FPE cells by any of the methods for mRNA isolation, for example as described Example 1.

Furthermore, any oligonucleotide pairs that flank a region of TS gene, as shown in SEQ ID NO: 11, may be used to carry out the methods of the invention. Primers hybridizing under stringent conditions to a region of the TS gene for use in the present invention will amplify a product between 20-1000 base pairs, preferably 50-100 base pairs, most preferably less than 100 base pairs.

The invention provides specific oligonucleotide primers pairs and oligonucleotide primers substantially identical thereto, that allow particularly accurate assessment of TS expression in FPE tissues. Preferable are oligonucleotide primers, TS-763F (SEQ ID NO: 3) and TS (SEQ ID NO: 4), (also referred to herein as the oligonucleotide primer pair TS) and oligonucleotide primers substantially identical thereto. The oliogonucleotide primers TS-763F (SEQ ID NO: 3) and TS, (SEQ ID NO: 4) have been shown to be particularly effective for measuring TS mRNA levels using RNA extracted from the FPE cells by any of the methods for mRNA isolation, for example as described Example 1.

This invention includes substantially identical oligonucleotides that hybridize under stringent conditions (as defined herein) to all or a portion of the oligonucleotide primer sequence of ERCC1-504F (SEQ ID NO: 1), its complement or ERCC1-574R (SEQ ID NO: 2), or its complement or oligonucleotide primer sequence of TS-763F (SEQ ID NO: 3), its complement or TS-825R (SEQ ID NO: 4), or its complement.

Under stringent hybridization conditions, only highly complementary, i.e., substantially similar nucleic acid sequences as defined herein hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides.

The hybridizing portion of the nucleic acids is typically at least about 10 (e.g., 15) nucleotides in length. The hybridizing portion of the hybridizing nucleic acid is at least about 80%, preferably at least about 95%, or most preferably about at least 98%, identical to the sequence of a portion or all of oligonucleotide primer ERCC1-504F (SEQ ID NO: 1), its complement or ERCC1-574R (SEQ ID NO: 2), or its complement or oligonucleotide primer TS-763F (SEQ ID NO: 3), its complement or TS-825R (SEQ ID NO: 4), or its complement.

Hybridization of the oligonucleotide primer to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5× Denhart's solution/1.0% SDS, and washing in 0.2×SSC/0.1% SDS at room temperature. Moderately stringent conditions include washing in 3×SSC at 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

Oligonucleotide primers disclosed herein are capable of allowing accurate assessment of TS and/or ERCC1 gene expression in a fixed or fixed and paraffin embedded tissue, as well as frozen or fresh tissue. This is despite the fact that RNA derived from FPE samples is more fragmented relative to that of fresh or frozen tissue. Thus, the methods of the invention are suitable for use in assaying TS and/or ERCC1 gene expression levels in FPE tissue where previously there existed no way to assay TS and/or ERCC1 gene expression using fixed tissues.

Genotoxic agents that can used in combination to a 5-FU and oxaliplatin based chemotherapy are those that form persistent genomic lesions and are preferred for use as chemotherapeutic agents in the clinical management of cancer. The rate of cellular repair of genotoxin-induced DNA damage, as well as the rate of cell growth via the cell division cycle, affects the outcome of genotoxin therapy. Unrepaired lesions in a cell's genome can impede DNA replication, impair the replication fidelity of newly synthesized DNA or hinder the expression of genes needed for cell survival. Thus, one determinant of a genotoxic agent's cytotoxicity (propensity for contributing to cell death) is the resistance of genomic lesions formed therefrom to cellular repair. Genotoxic agents that form persistent genomic lesions, e.g., lesions that remain in the genome at least until the cell commits to the cell cycle, generally are more effective cytotoxins than agents that form transient, easily repaired genomic lesions.

The genotoxin, Oxaliplatin, i.e., cis-oxalato(trans-1-1,2-cyclohexanediamine) platinum (II) is described in U.S. Pat. No. 4,169,846. Related patents include: U.S. Pat. No. 5,290,961; U.S. Pat. No. 5,298,642; U.S. Pat. No. 5,338,874; U.S. Pat. No. 5,420,319 and PCT/IB/00614. Oxaliplatin belongs to the class of platinum(II)-trans-1,2-diaminocyclohexane complexes which are currently in full development. Said complexes, or "dach" complexes are being clinically tested and are especially efficient against melanomae and tumors of the ovaries, uterus, stomach and intestine, etc. Other compounds that can be used to supplement 5-FU and oxaliplatin based chemotherapies can also include members analogs of oxaliplatin such as "dach" complexes and those that form covalent DNA adducts. In a preferred embodiment, the supplemental platinum compound used the present invention is oxaliplatin.

Tumors currently manageable by platinum coordination compounds include testicular, endometrial, cervical, gastric, squamous cell, adrenocortical and small cell lung carcinomas, along with medulloblastomas and neuroblastomas.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLES

Example 1

RNA Isolation from FPE Tissue

RNA is extracted from paraffin-embedded tissue by the following general procedure.

A. Deparaffinization and Hydration of Sections:

(1) A portion of an approximately 10 μM section is placed in a 1.5 mL plastic centrifuge tube.

(2) 600 μL, of xylene are added and the mixture is shaken vigorously for about 10 minutes at room temperature (roughly 20 to 25° C.).

(3) The sample is centrifuged for about 7 minutes at room temperature at the maximum speed of the bench top centrifuge (about 10-20,000×g).

(4) Steps 2 and 3 are repeated until the majority of paraffin has been dissolved. Two or more times are normally required depending on the amount of paraffin included in the original sample portion.

(5) The xylene solution is removed by vigorously shaking with a lower alcohol, preferably with 100% ethanol (about 600 μL) for about 3 minutes.

(6) The tube is centrifuged for about 7 minutes as in step (3). The supernatant is decanted and discarded. The pellet becomes white.

(7) Steps 5 and 6 are repeated with successively more dilute ethanol solutions: first with about 95% ethanol, then with about 80% and finally with about 70% ethanol.

(8) The sample is centrifuged for 7 minutes at room temperature as in step (3). The supernatant is discarded and the pellet is allowed to dry at room temperature for about 5 minutes.

B. RNA Isolation with Phenol-Chloroform (1) 400 μL guanidine isothiocyanate solution including 0.5% sarcosine and 8 dithiothreitol is added.

(2) The sample is then homogenized with a tissue homogenizer (Ultra-Turrax, IKA-Works, Inc., Wilmington, N.C.) for about 2 to 3 minutes while gradually increasing the speed from low speed (speed 1) to high speed (speed 5).

(3) The sample is then heated at about 95° C. for about 5-20 minutes. It is preferable to pierce the cap of the tube containing the sample with a fine gauge needle before heating to 95° C. Alternatively, the cap may be affixed with a plastic clamp or with laboratory film.

(4) The sample is then extracted with 50 μL 2M sodium acetate at pH 4.0 and 600 μL of phenol/chloroform/isoamyl alcohol (10:1.93:0.036), prepared fresh by mixing 18 mL phenol with 3.6 mL of a 1:49 isoamyl alcohol:chloroform solution. The solution is shaken vigorously for about 10 seconds then cooled on ice for about 15 minutes.

(5) The solution is centrifuged for about 7 minutes at maximum speed. The upper (aqueous) phase is transferred to a new tube.

(6) The RNA is precipitated with about 10 μL, glycogen and with 400 μL isopropanol for 30 minutes at −20° C.

(7) The RNA is pelleted by centrifugation for about 7 minutes in a benchtop centrifuge at maximum speed; the supernatant is decanted and discarded; and the pellet washed with approximately 500 μL of about 70 to 75% ethanol.

(8) The sample is centrifuged again for 7 minutes at maximum speed. The supernatant is decanted and the pellet air dried. The pellet is then dissolved in an appropriate buffer for further experiments (e.g., 50 pI. 5 mM Tris chloride, pH 8.0).

Example 2 mRNA Reverse Transcription and PCR

Reverse Transcription:

RNA was isolated from microdissected or non-microdissected formalin fixed paraffin embedded (FPE) tissue as illustrated in Example 1 and as previously described in U.S. application Ser. No. 09/469,338 filed Dec. 20, 1999, which is hereby incorporated by reference in its entirety. After precipitation with ethanol and centrifugation, the RNA pellet was dissolved in 50 ul of 5 mM Tris/Cl at pH 8.0. M-MLV Reverse Transcriptase will extend an oligonucleotide primer hybridized to a single-stranded RNA or DNA template in the presence of deoxynucleotides, producing a complementary strand. The resulting RNA was reverse transcribed with random hexamers and M-MLV Reverse Transcriptase from Life Technologies. The reverse transcription was accomplished by mixing 25 μl of the RNA solution with 25.5 μl of "reverse transcription mix" (see below). The reaction was placed in a thermocycler for 8 min at 26/C (for binding the random hexamers to RNA), 45 min at 42/C (for the M-MLV reverse transcription enzymatic reaction) and 5 min at 95/C (for heat inactivation of DNAse).

"Reverse transcription mix" consists of 10 ul 5× buffer (250 mM Tris-HCl, pH 8.3, 375 mM KCl, 15 mM MgCl2), 0.5 ul random hexamers (50 O.D. dissolved in 550 ul of 10 mM Tris-HCl pH 7.5) 5 ul 10 mM dNTPs (dATP, dGTP, dCTP and dTTP), 5 ul 0.1 M DTT, 1.25 ul BSA (3 mg/ml in 10 mM Tris-HCL, pH 7.5), 1.25 ul RNA Guard 24,800 U/ml (RNAse inhibitor) (Porcine #27-0816, Amersham Pharmacia) and 2.5 ul MMLV 200 U/ul (Life Tech Cat #28025-02).

Final concentrations of reaction components are: 50 mM Tris-HCl, pH 8.3, 75 mM KCl, 3 mM MgCl2, 1.0 mM dNTP, 1.0 mM DTT, 0.00375 mg/ml BSA, 0.62 U/ul RNA Guard and 10 U/ul MMLV.

PCR Quantification of mRNA Expression.

Quantification of ERCC1 cDNA and an internal control or house keeping gene (e.g., β-actin) cDNA was done using a fluorescence based real-time detection method (ABI PRISM 7700 or 7900 Sequence Detection System [TaqMan® ], Applied Biosystems, Foster City, Calif.) as described by Heid et al., (Genome Res 1996; 6:986-994); Gibson et al., (Genome Res 1996; 6:995-1001). In brief, this method uses a dual labelled fluorogenic TaqMan® oligonucleotide probe, (ERCC1-530Tc (SEQ ID NO: 5), $T_m$=70° C.; TS-781 (SEQ ID NO: 6), β-actin-611 (SEQ ID NO: 7)) that anneals specifically within the forward and reverse primers. Laser stimulation within the capped wells containing the reaction mixture causes emission of a 3' quencher dye (TAMRA) until the probe is cleaved by the 5' to 3' nuclease activity of the DNA polymerase during PCR extension, causing release of a 5' reporter dye (6FAM). Production of an amplicon thus causes emission of a fluorescent signal that is detected by the TaqMan®'s CCD (charge-coupled device) detection camera, and the amount of signal produced at a threshold cycle within the purely exponential phase of the PCR reaction reflects the starting copy number of the sequence of interest. Comparison of the starting copy number, of the sequence of interest with the starting copy number of the internal control gene provides a relative gene expression level. TaqMan® analyses yield levels that are expressed as ratios between two absolute measurements (gene of interest/internal control gene).

The PCR reaction mixture consisted 0.5 μl of the reverse transcription reaction containing the cDNA prepared as described above 600 nM of each oligonucleoride primers ERCC1-504F (SEQ ID NO:1, $T_m$=59° C.) and ERCC1-574R (SEQ ID NO: 2, $T_m$=58° C.) or oligonucleotide primers TS-763F (SEQ ID NO:3) and TS-825R (SEQ ID NO:4) 200 nM TaqMan® probe (SEQ ID NO:5 or SEQ ID NO: 6), 5 U AmpliTaq Gold Polymerase, 200 μM each dATP, dCTP, dGTP, 400 μM dTTP, 5.5 mM $MgCl_2$, and 1× Taqman Buffer A containing a reference dye, to a final volume of less than or equal to 25 μl (all reagents Applied Biosystems, Foster City, Calif.). Cycling conditions were, 95° C. for 10 min, followed by 45 cycles at 95° C. for 15 s and 60° C. for 1 min. Oligonucleotides used to quantify internal control gene β-Actin were β-Actin-592F (SEQ ID NO: 8) and β-Actin-651R (SEQ ID NO: 9).

Example 3

Determining the Uncorrected Gene Expression (UGE) for ERCC1

Two pairs of parallel reactions are carried out. The "test" reactions and the "calibration" reactions. FIG. 7. The ERCC1 amplification reaction and the β-actin internal control amplification reaction are the test reactions. Separate ERCC1 and β-actin amplification reactions are performed on the calibrator RNA template and are referred to as the calibration reactions. The TaqMan® instrument will yield four different cycle threshold (Ct) values: $Ct_{ERCC1}$ and $Ct_{\beta\text{-}actin}$ from the test reactions and $Ct_{ERCC1}$ and $Ct_{\beta\text{-}actin}$ from the calibration reactions. The differences in Ct values for the two reactions are determined according to the following equation:

$$\Delta Ct_{test} = Ct_{ERCC1} - Ct_{\beta\text{-}actin} \text{ (From the "test" reaction)}$$

$$\Delta Ct_{calibrator} = Ct_{ERCC1} - Ct_{\beta\text{-}actin} \text{ (From the "Calibration" Reaction)}$$

Next the step involves raising the number 2 to the negative ΔCt, according to the following equations.

$$2^{-\Delta Ct_{test}} \text{ (From the "test" reaction)}$$

$$2^{-\Delta Ct_{calibrator}} \text{ (From the "calibration" reaction)}$$

In order to then obtain an uncorrected gene expression for ERCC1 from the TaqMan® instrument the following calculation is carried out:

Uncorrected gene expression (UGE) for ERCC1=$2^{-\Delta Ct_{test}}/2^{-\Delta Ct_{calibrator}}$ Normalizing UGE with Known Relative ERCC1 Expression Levels The normalization calculation entails a multiplication of the UGE with a correction factor ($K_{ERCC1}$) specific to ERCC1 and a particular calibrator RNA. A correction factor $K_{ERCC1}$ can also be determined for any internal control gene and any accurately pre-quantified calibrator RNA. Preferably, the internal control gene β-actin and the accurately pre-quantified calibrator RNA, Human Liver Total RNA (Stratagene, Cat. #735017), are used. Given these reagents correction factor $K_{ERCC1}$ equals $1.54 \times 10^{-3}$.

Normalization is accomplished using a modification of the ΔCt method described by Applied Biosystems, the TaqMan® manufacturer, in User Bulletin #2 and described above. To carry out this procedure, the UGE of 6 different test tissues were analyzed for ERCC1 expression using the TaqMan® methodology described above. The internal control gene β-actin and the calibrator RNA, Human Liver Total RNA (Stratagene, Cat. #735017) was used.

The known relative ERCC1 expression level of each sample AG221, AG222, AG252, Adult Lung, PC3, AdCol was divided by its corresponding TaqMan® derived UGE to yield an unaveraged correction factor K.

$K_{unaveraged}$=Known Values/UGE

Next, all of the K values are averaged to determine a single $K_{ERCC1}$ correction factor specific for ERCC1, Human Liver Total RNA (Stratagene, Cat. #735017) from calibrator RNA and β-actin.

Therefore, to determine the Corrected Relative ERCC1 Expression in an unknown tissue sample on a scale that is consistent with pre-TaqMan® ERCC1 expression studies, one merely multiplies the uncorrected gene expression data (UGE) derived from the TaqMan® apparatus with the $K_{ERCC1}$ specific correction factor, given the use of the same internal control gene and calibrator RNA.

Corrected Relative ERCC1 Expression=UGE×$K_{ERCC1}$

A $K_{ERCC1}$ may be determined using any accurately pre-quantified calibrator RNA or internal control gene. Future sources of accurately pre-quantified RNA can be calibrated to samples with known relative ERCC1 expression levels as described in the method above or may now be calibrated against a previously calibrated calibrator RNA such as Human Liver Total RNA (Stratagene, Cat. #735017) described above.

For example, if a subsequent $K_{ERCC1}$ is determined for a different internal control gene and/or a different calibrator RNA, one must calibrate both the internal control gene and the calibrator RNA to tissue samples for which ERCC1 expression levels relative to that particular internal control gene have already been determined. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{ERCC1}$ specific to the different internal control gene and/or calibrator RNA.

Example 4

Determining the Uncorrected Gene Expression (UGE) for TS

Two pairs of parallel reactions are carried out. The "test" reactions and the "calibration" reactions. FIG. 8. The TS amplification reaction and the β-actin internal control amplification reaction are the test reactions. Separate TS and β-actin amplification reactions are performed on the calibrator RNA template and are referred to as the calibration reactions. The TaqMan® instrument wilt yield four different cycle threshold (Ct) values: $Ct_{TS}$ and $Ct_{\beta\text{-}actin}$ from the test reactions and $Ct_{TS}$ and $Ct_{\beta\text{-}actin}$ from the calibration reactions. The differences in Ct values for the two reactions are determined according to the following equation:

$\Delta Ct_{test} = Ct_{TS} - Ct_{\beta\text{-}actin}$ (From the "test" reaction)

$\Delta Ct_{calibrator} = Ct_{TS} - Ct_{\beta\text{-}actin}$ (From the "Calibration" Reaction)

Next the step involves raising the number 2 to the negative ΔCt, according to the following equations.

$2^{-\Delta Ct}_{test}$ (From the "test" reaction)

$2^{-\Delta Ct}_{calibrator}$ (From the "calibration" reaction)

In order to then obtain an uncorrected gene expression for TS from the TaqMan® instrument the following calculation is carried out:

Uncorrected gene expression (UGE) for $TS = 2^{-\Delta Ct}_{test} / 2^{-\Delta Ct}_{calibrator}$ Normalizing UGE with Known Relative TS Expression Levels The normalization calculation entails a multiplication of the UGE with a correction factor ($K_{TS}$) specific to TS and a particular calibrator RNA. A correction factor $K_{TS}$ can also be determined for any internal control gene and any accurately pre-quantified calibrator RNA. Preferably, the internal control gene β-actin and the accurately pre-quantified calibrator RNA, Universal PE RNA; Cat #4307281, lot #3617812014 from Applied Biosystems are used. Given these reagents correction factor $K_{TS}$ equals 12.6×

Normalization is accomplished using a modification of the ΔCt method described by Applied Biosystems, the TaqMan® manufacturer, in User Bulletin #2 and described above. To carry out this procedure, the UGE of 6 different previously published test tissues were analyzed for TS expression using the TaqMan® methodology described above. These tissue samples are described in Salonga, et al., Clinical Cancer Research, 6:1322-1327, 2000, which is hereby incorporated by reference in its entirety. The internal control gene β-actin and the calibrator RNA, Universal PE RNA; Cat #4307281, lot #3617812014 from Applied Biosystems was used.

The previously published relative TS expression level of each sample L7, L91, L121, L150, L220, L164 was divided by its corresponding TaqMan® derived UGE to yield an unaveraged correction factor K. Salonga, et al., Clinical Cancer Research, 6:1322-1327, 2000, incorporated herein by reference in its entirety.

$K_{unaveraged}$ = Known Values/UGE

Next, all of the K values are averaged to determine a single $K_{ERCC1}$ correction factor specific for TS, Applied Biosystems Universal PE RNA; Cat #1307281, lot #3617812014 calibrator RNA, and β-actin.

Therefore, to determine the Corrected Relative TS Expression in an unknown tissue sample on a scale that is consistent with pre-TaqMan® TS expression studies, one merely multiplies the uncorrected gene expression data (UGE) derived from the TaqMan® apparatus with the $K_{TS}$ specific correction factor, given the use of the same internal control gene and calibrator RNA.

Corrected Relative $TS$ Expression = UGE × $K_{TS}$

A $K_{TS}$ may be determined using any accurately pre-quantified calibrator RNA or internal control gene. Future sources of accurately pre-quantified RNA can be calibrated to samples with known relative ERCC1 expression levels as described in the method above or may now be calibrated against a previously calibrated calibrator RNA such as Universal PE RNA; Cat #4307281, lot #3617812014 from Applied Biosystems described above.

For example, if a subsequent $K_{TS}$ is determined for a different internal control gene and/or a different calibrator RNA, one must calibrate both the internal control gene and the calibrator RNA to tissue samples for which TS expression levels relative to that particular internal control gene have already been determined or published. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{TS}$ specific to the different internal control gene and/or calibrator RNA.

Example 5

Patient Selection and Chemotherapy Treatment

All patients were enrolled in the compassionate protocol 3C-98-3 at the University of Southern California Medical Center from 1998-2000 and received the following oxaliplatin/5-FU combination therapy regimen: 130 mg/m² oxaliplatin plus continuous infusion of 5-FU. All patients had failed a prior treatment with 5-FU and 60% (30/50) had failed an additional second line treatment with irinotecan (CPT-11). All patients showed active disease in stage IV colorectal cancer at time of protocol entry.

Clinical Evaluation and Response Criteria

During chemotherapy, weekly evaluations were recorded for performance status, weight, abdominal pain, complete blood counts, and serum creatinine and blood urea nitrogen levels. Tumor burden is measured using computed tomography (CT). A bi-dimensionally measurable tumor mass was required at the time of protocol entry. Responders to therapy were classified as those patients whose tumor burden was decreased by 50% or more for at least 6 weeks. Non-responders included those with stable disease or cancer progression.

Survival was computed as the number of days from the initiation of chemotherapy with 5-FU/oxaliplatin to death of any cause. Patients who were alive at the last follow-up evaluation were censored at that time.

Statistical Analysis

TaqMan® analyses yield levels that are expressed as ratios between two absolute measurements (gene of interest:internal reference gene). The Mann-Whitney test and Kruskal-Wallis test were used to evaluate the associations of TS and ERCC1 expression (as continuous variables) with patients demographics. Zar, Biostatistical Analysis. Prentice-Hall, Inc Englewood Cliffs, N.J. (1974), pp. 109-114 and 139-142, respectively. The maximal chi-square method of Miller and Sigmund (Biometrics 38: 1011-1016, 1982) and Halpern (Biometrics 38: 1017-1023, 1982), was adapted to determine which cut-off threshold level best dichotomized patients into low and high TS and ERCC1 expression subgroups. Pearson's chi-square test was used to assess the associations between the dichotomized molecular markers and to response to chemotherapy Zar, Biostatistical Analysis. Prentice-Hall, Inc Englewood Cliffs, N.J. (1974), pp. 59-68. Hazard ratios were used to calculate the relative risks of death. Schulman, Infection Control & Hospital Epidemiology, 18:65-73, 1997. These calculations were based on the Pike estimate, with the use of the observed and expected number of events as calculated in the log-rank test statistic (Pike, J R Stat Soc Series A 135: 201-203, 1972). To determine a P value that would be interpreted as a measure of the strength of the association based art the maximal chi-square analysis, 1000 boot-strap-like simulations were used to estimate the distribution of the maximal chi-square statistics under the hypothesis of no association. (Halpern, Biometrics 38: 1017-1023, 1982). The level of significance was set to p<0.05.

Demographics and Patients Available for Response and Survival Evaluation

A total of 50 patients, consisting of 14 (28%) women and 36 (72%) men, with a median age of 59 (min.: 34; max.: 83) years were evaluated in this study. The ethnic backgrounds of this group included 39 Caucasians, 6 Hispanics, 3 Asians, and 2 African-Americans. All 50 patients were assessable to associate TS expression and ERCC1 expression levels with survival. Forty-five (90%) were assessable to test the association of this molecular parameters with response by above cited criteria.

TS Expression Levels and ERCC1 Expression Levels

Total mRNA was isolated from microdissected FPE pretreatment tumor samples, and relative mRNA expression levels of ERCC1: β-actin and or TS:β-actin were measured using quantitative RT-PCR. A method for mRNA isolation from such samples is described in Example 1 and in U.S. patent application Ser. No. 09/469,338, filed Dec. 20, 1999, and is hereby incorporated by reference in its entirety. A reverse transcription/polymerase chain reaction (RT/PCR)-based assay system was used to determine the level of expression of ERCC1, and β-actin, as described in Example 2. Corrected relative ERCC1 and/or TS expression was deterimined as described in Examples 3 and 4, respectively.

TS gene expression was detectable in all 50 samples analyzed. The median corrected TS expression, relative to the housekeeping gene, O-Actin, was $3.4 \times 10^{-3}$ (min.: $0.18 \times 10^{-3}$; max.: $11.5 \times 10^{-3}$). Corrected ERCC1 gene expression was detectable in 47 (94%) samples analyzed. The median corrected ERCC1 gene expression was $2.53 \times 10^{-3}$ (min.: 0.00; max.: $14.61 \times 10^{-3}$). When analyzed by gender, age, and ethnic origin, no significant differences in corrected TS and ERCC1 mRNA expression were found.

Survival in Relation to TS Expression

With a median follow-up period of 10.5 months (95% C.I.: 1.8, 21.2) for the 50 patients analyzed in this study, the median survival was 8.4 months (95% C.I.: 6.4, 12.3). Using a TS threshold value of $7.5 \times 10^{-3}$, 43 (86%) patients had a low corrected TS expression level, and 7 (14%) patients had a high corrected TS expression level. The log-rank test was used to evaluate the association between corrected TSgene expression and survival. The respective survival curves are presented in FIG. 1 and show a median survival of 10.2 months (95% C.I.:7.4, 15.1) in the low corrected TS expressor group, and 1.5 months (95% C.I.:1.1, 2.1) in the high corrected TS expression group (P<0.001; Logrank Test). The probability of survival at 6 months was 0.77 for patients with corrected TS expression≤$7.5 \times 10^{-3}$ compared to 0.00 for the high expressor group. Patients with corrected TS levels >$7.5 \times 10^{-3}$ had a 8.4 (95% CI: 2.63, 27.13) fold increased relative risk of dying compared to patients with TS levels ≤$7.5 \times 10^{-3}$ in the univariate analysis (p<0.001, FIG. 4).

Survival in Relation to ERCC1 Expression

Figure 2:
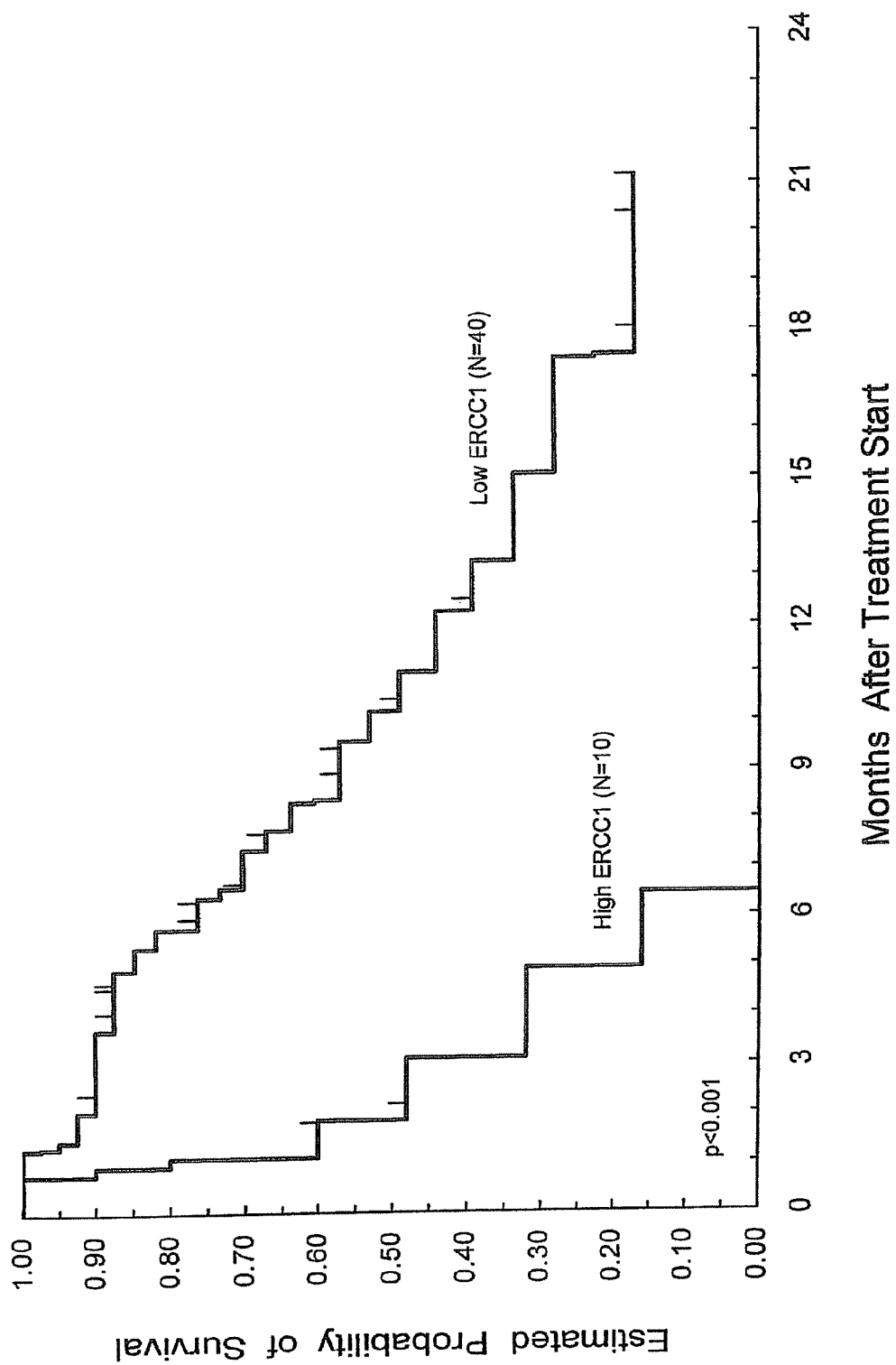
FIG. 2 is a graph showing the estimated probability of survival and survival in months of colorectal adenocarcinoma tumor carrying patients with high (greater than about 4.9× $10^{-3}$ times β-actin gene expression; n=10) and low (less than about 4.9×$10^{-3}$ times β-actin gene expression; n=40) corrected ERCC1 expression levels receiving 5-FU and oxaliplatin therapeutic regimen.

Using $4.9 \times 10^{-3}$ as a threshold, 40 (80%) had a low corrected ERCC1 expression and 10 (20%) had a high corrected ERCC1 expression. FIG. 2 displays a Kaplan Meier plot of the estimated probability of survival versus corrected ERCC1 expression levels, and shows a median survival of 10.2 months (95% C.I.:7.8, 15.1) for the low expressor group and 1.9 months (95% C.I.:1.1, 4.9) for the high expressor group (P<0.001; Logrank Test). The probability of survival at 6 months was 0.76 for patients with corrected ERCC1 expression ≤$4.9 \times 10^{-3}$ compared to 0.16 for patients with corrected ERCC1 expression >$4.9 \times 10^{-3}$. Patients with corrected ERCC1 levels >$4.9 \times 10^{-3}$ had a 4.8 (95% CI: 2.09, 15.88) fold increased relative risk of dying compared to patients with corrected ERCC1 levels ≤$4.9 \times 10^{-3}$ in the univariate analysis (p<0.001; FIG. 4).

Survival in Relation to Combined ERCC1 and TS Expression

Figure 3:
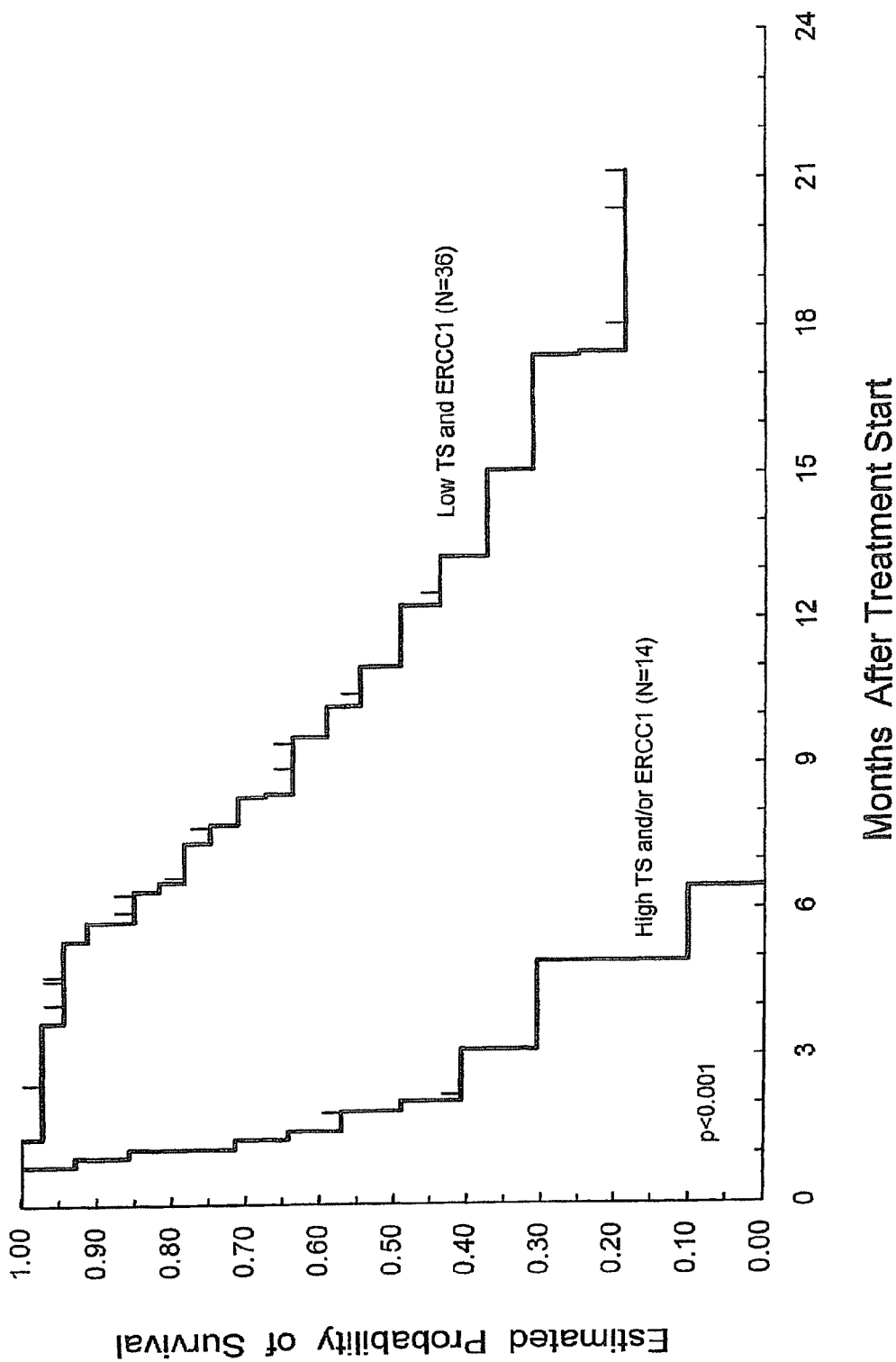
FIG. 3 is a graph showing the estimated probability of survival and survival in months of colorectal adenocarcinoma tumor carrying patients with high (TS expression greater than about 7.5×$10^{-3}$ times β-actin gene expression and ERCC1 greater than about 4.9×$10^{-3}$ times β-actin gene expression; n=14) and low (TS expression less than about 7.5×$10^{-3}$ times β-actin gene expression and ERCC1 less than about 4.9×$10^{-3}$ times β-actin gene expression; n=36) corrected TS and ERCC1 expression levels receiving 5-FU and oxaliplatin therapeutic regimen.
Figure 6:
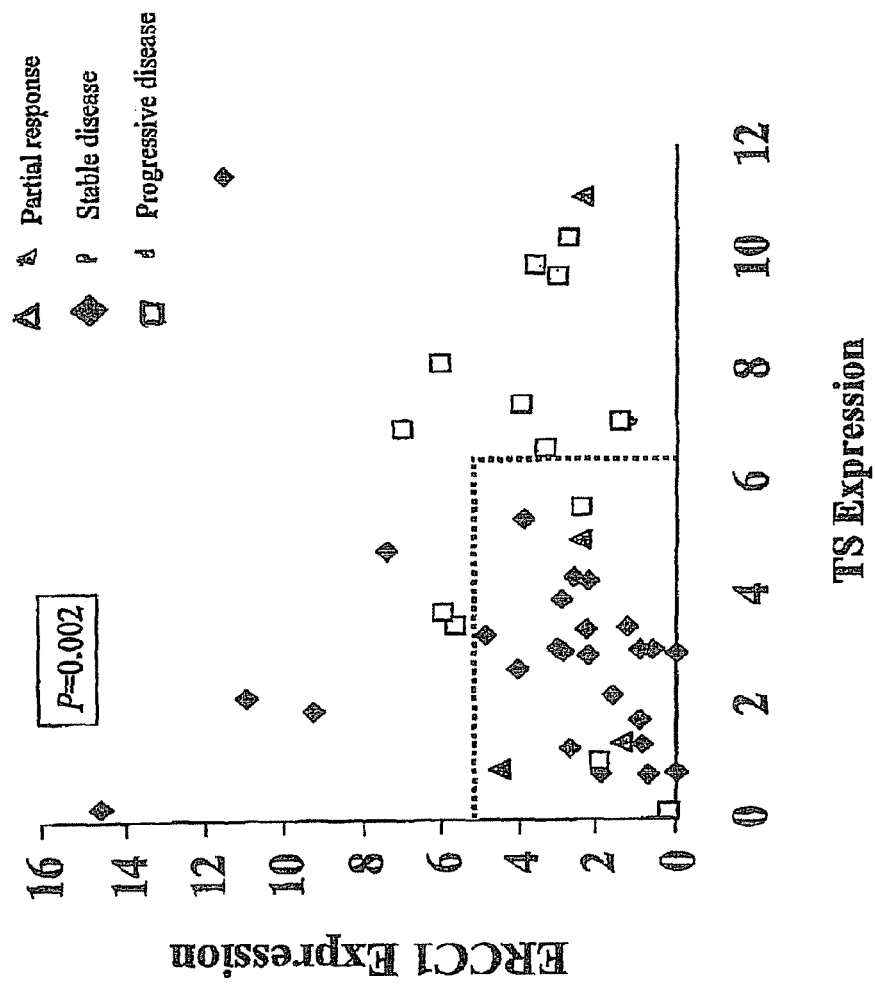
FIG. 6 is a graph showing the response of colorectal adenocarcinoma tumor carrying patients treated with a 5-FU and oxaliplatin chemotherapeutic regimen relative to. Patients were classified into those with progressive disease (PD), partial response (PR), and stable disease (SD). Patients with low levels of both TS and ERCC1 expression had the best response.

Low corrected TS and ERCC1 expression levels were detected in 36 (72%) of the patients, and 14 (28%) patients had high corrected TS and/or ERCC1 expression level. Patients with low expression levels for both genes had a significant superior survival. The median survival was 11.1 months (95% C.I.:8.4, 17.5) for the low corrected TS and ERCC1 expressors, and 1.9 months (95% C.I.:1.1, 4.9) for the high corrected TS and/or ERCC1 expressors (P<0.001, Logrank Test; FIG. 3). Patients with low corrected expression levels for both genes had a probability of survival at 6 months of 0.85 compared to 0.10 for the patients with a high corrected expression level for at least one gene, TS or ERCC1. The relative risk of dying for patients with an increased corrected expression for at least one gene (TS or ERCC1) was 7.12 (95% CI: 2.60, 19.52) compared to patients, which showed low expression levels for both genes in the tumor (P<0.001; FIG. 4). TS and ERCC1 mRNA expression are independent of each other as revealed by the stratified analysis (FIG. 5).

Association of Response with TS and ERCC1 Gene Expression Levels.

The median corrected TS expression level was $3.4 \times 10^{-3}$ (min.: $0.18 \times 10^{-3}$; max.: $11.50 \times 10^{-3}$) for the 45 measurable patients and is identical to the entire 50 patient-cohort. When responses were analyzed by segregating tumors into low- and high TS expressors, three out of four (75%) partial responders, 26 of 27 (96%) of patients with stable disease, and 9 of 14 (64%) of patients with progressive disease had a low corrected TS expression (P=0.02; Fisher's Exact Test; FIG. 9).

The median corrected ERCC1 expression level was $2.7 \times 10^{-3}$ (min.: 0.00; max.: $14.61 \times 10^{-3}$) for the 45 measurable patients and not significantly different to the entire 50 patient-cohort. However the ERCC1 expression level was not statistically significant associated with response to chemotherapy (p=0:29, Fisher's Exact Test).

What is claimed is:

1. A method of treating a tumor with a chemotherapeutic regimen comprising:
   (a) isolating mRNA from a fixed tumor tissue sample;
   (b) subjecting the mRNA to reverse transcriptase-polymerase chain reaction (RT-PCR) amplification using
      (i) a pair of oligonucleotide primers capable of amplifying a region of the Excision Repair Cross-Complementing (ERCC1) gene, and
      (ii) a pair of oligonucleotide primers capable of amplifying a region of the Thymidylate Synthase (TS) gene,
   to obtain an ERCC1 and a TS amplified sample;
   (c) determining the levels of TS and ERCC1 mRNA expression in the amplified samples relative to the level of mRNA expression of an internal control gene; and
   (d) treating the tumor with a chemotherapeutic regimen comprising
      (i) a platinum-based genotoxic agent when the determined level of ERCC1 mRNA expression is below a predetermined threshold value; and/or
      (ii) a fluorouracil-based therapeutic when the determined level of TS mRNA expression is below a predetermined threshold value.

2. The method of claim 1, wherein the tumor tissue sample is fixed and embedded in paraffin.

3. The method of claim 2, further comprising subjecting the fixed, paraffin-embedded tumor tissue sample to laser capture microdissection prior to isolating mRNA.

4. The method of claim 1, wherein mRNA is isolated using a method comprising heating the tumor tissue sample in a solution comprising an effective concentration of a chaotropic compound at a temperature of about 50 to about 100° C. for about 5 to about 120 minutes.

5. The method of claim 3, wherein the sample is heated at about 75 to about 100° C.

6. The method of claim 3, wherein the sample is heated at about 95° C. for about 5 to about 20 minutes.

7. The method of claim 1, wherein:
(a) for amplifying the region of the ERCC1 gene the oligonucleotide primer pair consists of an oligonucleotide represented by the sequence of SEQ ID NO:1 or a sequence at least 95% identical thereto and an oligonucleotide represented by the sequence of SEQ ID NO:2 or a sequence at least 95% identical thereto; and
(b) for amplifying the region of the TS gene the oligonucleotide primer pair consists of an oligonucleotide represented by the sequence of SEQ ID NO:3 or a sequence at least 95% identical thereto and an oligonucleotide represented by the sequence of SEQ ID NO:4 or a sequence at least 95% identical thereto.

8. The method of claim 1, wherein:
(a) for amplifying the region of the ERCC1 gene the oligonucleotide primer pair consists of an oligonucleotide represented by the sequence of SEQ ID NO:1 and an oligonucleotide represented by the sequence of SEQ ID NO:2; and
(b) for amplifying the region of the TS gene the oligonucleotide primer pair consists of an oligonucleotide represented by the sequence of SEQ ID NO:3 and an oligonucleotide represented by the sequence of SEQ ID NO:4.

9. The method of claim 1, wherein the tumor is a breast, head and neck, lung, esophageal, colorectal, testicular, endometrial, cervical, gastric, gastrointestinal tract, squamous cell, adrenocortical or small cell lung tumor, a carcinoma or sarcoma of the respiratory, gastrointestinal or reproductive tract or of the central nervous system, a medulloblastoma or a neuroblastoma tumor.

10. The method of claim 1, wherein the tumor is a small cell lung carcinoma.

11. The method of claim 1, wherein the tumor is a colorectal adenocarcinoma.

12. The method of claim 1, wherein the platinum-based genotoxic agent is oxaliplatin, cisplatin, carboplatin, a "dach" complex, or a combination thereof.

13. The method of claim 1, wherein the tumor is treated with a chemotherapeutic regimen comprising 5-fluorouracil and oxaliplatin.

14. The method of claim 1, wherein the internal control gene is the β-actin gene.

15. The method of claim 14, wherein the predetermined threshold level of ERCC1 mRNA expression is about $4.9 \times 10^{-3}$ times the expression level of the β-actin mRNA.

16. The method of claim 14, wherein the threshold level of TS gene expression is about $7.5 \times 10^{-3}$ times the mRNA expression level of the β-actin mRNA.

* * * * *

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 1
gggaatttgg cgacgtaatt c                                              21

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 2
gcggaggctg aggaacga                                                  18

<210> SEQ ID NO 3
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 3
ggcctcggtg tgcctttt                                                  17

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 4
gatgtgcgca atcatgtacg t                                              21

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide Probe

<400> SEQUENCE: 5
cacaggtgct ctggcccagc acata                                          25

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 6
aacatcgcca gctacgccct gc                                             22

<210> SEQ ID NO 7
<211> LENGTH: 18
<212> TYPE: DNA

```
<213> ORGANISM: Artificial Sequence
<220> FEATURE:
<223> OTHER INFORMATION: Oligonucleotide Probe

<400> SEQUENCE: 7
accaccacgg ccgagcgg                                                    18

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide Probe

<400> SEQUENCE: 8
tgagcgcggc tacagctt                                                    18

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 9
tccttaatgt cacgcacgat tt                                               22

<210> SEQ ID NO 10
<211> LENGTH: 1097
<212> TYPE: DNA
<213> ORGANISM: Homo sapiens

<400> SEQUENCE: 10
aagtgctgcg agccctgggc cacgctggcc gtgctggcag tgggccgcct cgatccctct      60
gcagtctttc ccttgaggct ccaagaccag caggtgaggc ctcgcggcgc tgaaaccgtg     120
aggcccggac cacaggctcc agatggaccc tgggaaggac aaagaggggg tgccccagcc     180
ctcagggccg ccagcaagga agaaatttgt gataccccct gacgaggatg aggtccctcc     240
tggagtggcc aagcccttat tccgatctac acagagcctt cccactgtgg cacctcggc      300 ccaggcggcc cctcagacct acgccgaata tgccatctca cagcctctgg aaggggctgg     360
ggccacgtgc cccacagggt cagagcccct ggcaggagag acgcccaacc aggccctgaa     420
acccggggca aaatccaaca gcatcattgt gagccctcgg cagaggggca atcccgtact     480
gaagttcgtg cgcaatgtgc cctgggaatt tggcgacgta attcccgact atgtgctggg     540
ccagagcacc tgtgccctgt tcctcagcct ccgctaccac aacctgcacc cagactacat     600
ccatgggcgc tgcagagcc tggggaagaa cttcgccttg cgggtcctgc ttgtccaggt     660
ggatgtgaaa gatccccagc aggccctcaa ggagctggct aagatgtgta tcctggccga     720
ctgcacattg atcctcgcct ggagccccga ggaagctggg cggtacctgg agacctacaa     780
ggcctatgag cagaaaccag cggacctcct gatggagaag ctagagcagg acttcgtctc     840
ccgggtgact gaatgtctga ccaccgtgaa gtcagtcaac aaaacggaca gtcagaccct     900
cctgaccaca tttggatctc tggaacagct catcgccgca tcaagagaag atctggcctt     960
atgcccaggc ctgggccctc agaaagcccg gaggctgttt gatgtcctgc acgagccctt    1020
cttgaaagta ccctgatgac cccagctgcc aaggaaaccc ccagtgtaat aataaatcgt    1080
cctcccaggc caggctc                                                  1097

<210> SEQ ID NO 11
```

-continued

```
<211> LENGTH: 1536
<212> TYPE: DNA
<213> ORGANISM: Homo sapiens

<400> SEQUENCE: 11
gggggggggg ggaccacttg gcctgcctcc gtcccgccgc gccacttggc ctgcctccgt        60
cccgccgcgc cacttcgcct gcctccgtcc cccgcccgcc gcgccatgcc tgtggccggc       120
tcggagctgc cgcgccggcc cttgccccccc gccgcacagg agcgggacgc cgagccgcgt      180
ccgccgcacg gggagctgca gtacctgggg cagatccaac acatcctccg ctgcggcgtc       240
aggaaggacg accgcacggg caccggcacc ctgtcggtat tcggcatgca ggcgcgctac       300
agcctgagag atgaattccc tctgctgaca accaaacgtg tgttctggaa gggtgttttg       360
gaggagttgc tgtggtttat caagggatcc acaaatgcta aagagctgtc ttccaaggga       420
gtgaaaatct gggatgccaa tggatcccga gactttttgg acagcctggg attctccacc       480
agagaagaag gggacttggg cccagtttat ggcttccagt ggaggcattt tggggcagaa       540
tacagagata tggaatcaga ttattcagga cagggagttg accaactgca aagagtgatt       600
gacaccatca aaaccaaccc tgacgacaga agaatcatca tgtgcgcttg aatccaaga       660 gatcttcctc tgatggcgct gcctccatgc catgccctct gccagttcta tgtggtgaac       720
agtgagctgt cctgccagct gtaccagaga tcgggagaca tgggcctcgg tgtgcctttc       780
aacatcgcca gctacgccct gctcacgtac atgattgcgc acatcacggg cctgaagcca       840 ggtgactttta tacacacttt gggagatgca catatttacc tgaatcacat cgagccactg       900
aaaattcagc ttcagcgaga acccagacct ttcccaaagc tcaggattct tcgaaaagtt       960
gagaaaattg atgacttcaa agctgaagac tttcagattg aagggtacaa tccgcatcca      1020
actattaaaa tggaaatggc tgtttagggt gctttcaaag gagcttgaag gatattgtca      1080
gtctttaggg gttgggctgg atgccgaggt aaaagttctt tttgctctaa aagaaaaagg      1140
aactaggtca aaaatctgtc cgtgacctat cagttattaa tttttaagga tgttgccact      1200
ggcaaatgta actgtgccag ttctttccat aataaaaggc tttgagttaa ctcactgagg      1260
gtatctgaca atgctgaggt tatgaacaaa gtgaggagaa tgaaatgtat gtgctcttag      1320
caaaaacatg tatgtgcatt tcaatcccac gtacttataa agaaggttgg tgaatttcac      1380
aagctatttt tggaatattt ttagaatatt ttaagaattt cacaagctat tccctcaaat      1440
ctgagggagc tgagtaacac catcgatcat gatgtagagt gtggttatga actttatagt      1500
tgttttatat gttgctataa taaagaagtg ttctgc                                1536
```